US009676621B2

(12) United States Patent
Chen et al.

(10) Patent No.: US 9,676,621 B2
(45) Date of Patent: Jun. 13, 2017

(54) GRAPHENE-BASED FIELD-EFFECT TRANSISTOR BIOSENSORS

(75) Inventors: Junhong Chen, Kenosha, WI (US); Shun Mao, Milwaukee, WI (US); Ganhua Lu, Milwaukee, WI (US)

(73) Assignee: UWM Research Foundation, Inc., Milwaukee, WI (US)

( * ) Notice: Subject to any disclaimer, the term of this patent is extended or adjusted under 35 U.S.C. 154(b) by 711 days.

(21) Appl. No.: 13/399,288

(22) Filed: Feb. 17, 2012

(65) Prior Publication Data

US 2012/0214172 A1  Aug. 23, 2012

Related U.S. Application Data

(60) Provisional application No. 61/444,395, filed on Feb. 18, 2011.

(51) Int. Cl.
*G01N 27/414* (2006.01)
*B82Y 15/00* (2011.01)

(52) U.S. Cl.
CPC .......... *B82Y 15/00* (2013.01); *G01N 27/4145* (2013.01); *G01N 27/4146* (2013.01)

(58) Field of Classification Search
CPC ..................... G01N 27/4145; G01N 27/4146
See application file for complete search history.

(56) References Cited

U.S. PATENT DOCUMENTS

| 5,521,289 | A | 5/1996 | Hainfeld et al. |
| 6,258,254 | B1 | 7/2001 | Miyamoto et al. |
| 7,208,587 | B2 | 4/2007 | Mirkin et al. |
| 7,235,170 | B2 | 6/2007 | Watanabe et al. |
| 7,465,953 | B1* | 12/2008 | Koh et al. .......................... 257/9 |
| 8,476,510 | B2* | 7/2013 | Swager ............... C01B 31/0213 257/40 |
| 2006/0205013 | A1 | 9/2006 | Shim et al. |
| 2007/0048796 | A1 | 3/2007 | Kubo et al. |
| 2008/0009002 | A1* | 1/2008 | Gruner ................... B82Y 15/00 435/6.11 |
| 2009/0057650 | A1* | 3/2009 | Lieber et al. .................... 257/24 |
| 2010/0025660 | A1 | 2/2010 | Jain et al. |
| 2010/0053624 | A1 | 3/2010 | Yoo et al. |
| 2010/0178464 | A1 | 7/2010 | Choi et al. |
| 2011/0042813 | A1* | 2/2011 | Crain et al. .................... 257/746 |
| 2011/0057168 | A1* | 3/2011 | Kobayashi ............. B82Y 10/00 257/24 |

(Continued)

OTHER PUBLICATIONS

Abe, M. et al. "Quantitative Detection of Protein using a Top-gate Carbon Nanotube Field Effect Transistor.", The Journal of Physical and Colloid Chemistry, 2007, p. 8667, 111.

(Continued)

*Primary Examiner* — Melanie Y Brown
(74) *Attorney, Agent, or Firm* — Michael Best & Friedrich LLP

(57) ABSTRACT

The disclosure provides a field-effect transistor (FET)-based biosensor and uses thereof. In particular, to FET-based biosensors using thermally reduced graphene-based sheets as a conducting channel decorated with nanoparticle-biomolecule conjugates. The present disclosure also relates to FET-based biosensors using metal nitride/graphene hybrid sheets. The disclosure provides a method for detecting a target biomolecule in a sample using the FET-based biosensor described herein.

19 Claims, 17 Drawing Sheets

(56) References Cited

U.S. PATENT DOCUMENTS

| | | | |
|---|---|---|---|
| 2011/0104442 A1 | 5/2011 | Yoon et al. | |
| 2011/0210314 A1 | 9/2011 | Chung et al. | |
| 2011/0227000 A1* | 9/2011 | Ruoff | B82Y 30/00 252/502 |
| 2011/0309334 A1 | 12/2011 | Chang et al. | |
| 2012/0058350 A1 | 3/2012 | Long et al. | |
| 2012/0107593 A1* | 5/2012 | Luo | G01N 27/4145 428/220 |
| 2012/0153262 A1* | 6/2012 | Paranjape | B82Y 10/00 257/24 |
| 2012/0214172 A1 | 8/2012 | Chen et al. | |
| 2012/0220053 A1* | 8/2012 | Lee | H01L 29/4908 436/501 |
| 2013/0040283 A1* | 2/2013 | Star | G01N 27/127 435/5 |
| 2014/0159040 A1 | 6/2014 | Dimitrakopoulos et al. | |
| 2014/0162375 A1 | 6/2014 | Afzali-Ardakani et al. | |

OTHER PUBLICATIONS

Allen, B.L. et al. "Carbon Nanotube Field-Effect-Transistor-Based Biosensors.", Advanced Materials, 2007, p. 1439-1451, 19.

Avasarala, B. et al. "Electrochemical oxidation behavior of titanium nitride based electrocatalysts under PEM fuel cell conditions.", Electrochimica Acta, 2010, p. 9024-9034, 55.

Bedioui, F. et al. "Comment on Electrochemical Detection of Peroxynitrite Using a Biosensor Based on a Conducting Polymer—Manganese Ion Complex.", Analytical Chemistry, 2011, p. 5463-5464, 83.

Braun, C. et al. "Ca3N2 and Mg3N2: Unpredicted High-Pressure Behavior of Binary Nitrides.", Journal of the American Chemical Society, 2011, p. 4307-4315, 133.

Bunch, J.S. et al. "Electrochemical Resonators from Graphene Sheets.", Science, 2007, p. 490, 315.

Campos-Delgado, J. et al. "Bulk Production of a New Form of sp2 Carbon: Crytalline Graphene Nanoribbons.", Nano Letters, 2008, p. 2773-2778, 8, 9.

Cao, A. et al. "Afacile One-step Method to Produce Grraphene-CdS Quantum Dot Nancomposites as Promising Optoelectronic Materials.", Advanced Materials, 2010, p. 103-106, 22.

Chakraborty, S. et al. "Amperometric biosensing of glutamate using carbon nanotube based electrode.", Electrochemistry Communications, 2007, p. 1323-1330, 9.

Chen, X. et al. "Synthesis of "clean" and well-dispersive Pd Nanoparticles with excellent electrocatalytic property on graphene oxide." Journal of the American Chemical Society, 2011, p. 3693-3695, 133.

Chen, J.H. et al. "Controlled Decoration of Carbon Nanotubes with Nanoparticles.", Nanotechnology, 2006, p. 2891, 17.

Chen, J.H. et al. "Intrinsic and Extrinsic Performance Limits of Graphene Devices on SiO2.", Nature Nanotechnology, 2008, p. 206, 3.

Chen, R.J. et al. "Noncovalent functionalization of carbon nanotubes for highly specific electronic biosensors.", Proceedings of the National Academy of Sciences, 2003, p. 4984-4989, 100, 9.

Choucair, M. et al. "Gram-scale production of graphene based on solvothermal synthesis and sonication.", Nature Nanotechnology, 2009, p. 30-33, 4.

Ci, L. et al. "Controlled Nanocutting of Graphene.", Nano Research, 2008, p. 116-122, 1.

Cote, L.J. et al. "Flash Reduction and Patterning of Graphite Oxide and Its Polymer Composite.", Journal of the American Chemistry Society, 2009, p. 11027-11033, 131.

Cui, Y et al. "Nanowire Nanosensors for Highly Sensitive and Selective Detection of Biological and Chemical Species.", Science, 2001, p. 1289-1292, 293.

Dikin, D.A. et al. "Preparation and Characterization of Graphene Oxide Paper.", Nature, 2007, p. 457-461, 448.

Dong, X.C. et al. "Electrical Detection of DNA Hybridization with Single-Base Specificity using Transistors Based on CVD-Grown Graphene Sheets.", Advanced Materials, 2010, 22, 1.

Dong, X.C. et al. "Electrical Detection of Femtomolar DNA via Gold-Nanoparticle Enhancement in Carbon-Nanotube-Network Field-Effect Transistors.", Advanced Materials, 2008, p. 2389-2393, 20.

Du, X. et al. "Approaching ballistic transport in suspended graphene.", Nature Nanotechnology, 2008, p. 491-497, 5.

Farrow, B. et al. "CdSe Quantum Dot Sensitized Solar Cells. Shuttling Electrons Through Stacked Carbon Nanocups.", Journal of the American Chemical Society 2009, p. 11124-11131, 131.

Fischer, A. et al. "Synthesis of Ternary Metal Nitride Nanoparticles Using Mesoporous Carbon Nitride as Reactive Template.", ACS Nano 2008, p. 2489-2496, 2, 12.

Gao, L. et al. "Crystallographic Tailoring of Graphene by Nonmetal SIO2 Nanoparticles.", Journal of the American Chemical Society, 2012, p. 13934-13936, 131.

Geim, A.K. "Graphene: Status and Prospects.", Science, 2009.

Geim, A.K. et al. "The Rise of Graphene.", Nature Materials, 2007, 6, 183.

Geng, D. et al. "High Oxygen-Reduction Activity and Durability of Nitrogen-Doped Graphene.", Energy and Environmental Science, 2011, p. 760-764, 4.

Giardi, M.T. et al. "Optical biosensors for environmental monitoring based on computational and biotechnological tools for engineering the photosynthetic D1 protein of *Chlamydomonas reinhardtii*.", Biosensors and Bioelectronics, 2009, p. 294-300, 25, 2.

Guijarro, N. et al. "Direct Correlation between Ultrafast Injection and Photoanode Performance in Quantum ot Sensitized Solar Cells.", Journal of Physical Chemistry, 2010, p. 22352-22360, 114.

Guo, S. et al. "Three-Dimensional Pt-onPd Bimetallic Nanodendrites Supported on Graphene Nanosheet: Facile Synthesis and Used as an Advanced Nanoelectrocatalyst for Methanol Oxidation.", ACS Nano, 2010, p. 547-555, 4, 1.

Guo, C.X. et al. "Layered Graphene/Quantum Dots for Photovoltaic Devices.", Angewandte Chemie International Edition, 2001, p. 3014-3017, 49.

Higgins, V.J. "Application of genome-wide expression analysis to identify molecular markers useful in monitoring industrial fermentations.", Applied and Environmental Microbiology, 2003, p. 7535-7540, 69.

Hong, S. et al "A Flexible Approach to Mobility.", Nature Nanotechnology, 2007, 2, 207.

Hu, P.A. et al. "Carbon Nanostructure-Based Field-Effect Transistors for Label-Free Chemical/Biological Sensors.", Sensors, 2010, p. 5133-5159, 10.

Hummers, W. et al. "Preparation of Graphitic Oxide.", American Chemistry Society, 1958, p. 1339, 80.

Jain, K.K. "Applications of Nanobiotechnology in Clinical Diagnostics.", Clinical Chemistry, 2007, p. 2002-2009, 53, 11.

Jiang, Q.W. et al. "Highly ordered TiN nantube arrays as counter electrodes for dye-sensitized solar cells.", Chemical Communications, 2009, p. 6720-6722.

Jiang, Q.W. et al. "Surface-Nitrided nickel with bifunctional structure as low-cost counter electrode for dye-sensitized solar cells.", Journal of Physical Chemistry C, 2010, p. 13397-13401, 114.

Jun, Y.S. et al. "Mesoporous, 2D Hexagonal Carbon Nitride and Titanium Nitride/Carbon Composites.", Advanced Materials 2009, p. 4270-4274, 21.

Jun, Y. et al. "A general phase-transfer protocol for metal ions and its application in nanocrystal synthesis.", Nature Materials, 2009, p. 683-689, 8.

Jung, I. et al. "Tunable Electrical Conductivity of Individual Graphene Oxide Sheets Reduced at "Low" Temperatures.", Nano Letters, 2008, 4283, 8.

Kim, J.P. et al. "Enhancement of Sensitivity and specificity by surface modification of carbon nanotubes in diagnosis of prostate cancer based on carbon nanotube field effect transistors.", Biosensors and Bioelectronics, 2009, p. 3372-2278, 24.

(56) References Cited

OTHER PUBLICATIONS

Kong, B.S. et al. "Layer-by-Layer assembly of graphene and gold nanoparticles by vacuum filtration and spontaneous reduction of gold ions.", Chemical Communications, 2009, p. 2174-2176.

Kovtyukhova, N. et al. "Layer-by-Layer Assembly of Ultrathin Composites Films from Micron-Sized Graphite Oxide Sheets and Polycations.", Chemistry Materials, 1999, p. 771-778, 11.

Langford, J.I. et al. "Scherrer after Sixty Years: A Survey and Some New Results in the Determination of Crystallite Size.", Journal of Applied Crystallography, 1978, p. 102-113, 11.

Lee, S.M. et al. "Expression of heat shock protein and hemoglobin genes in Chironomus tentans (Diptera, chironomidae) larvae exposed to various environmental pollutants: A potential biomarker of freshwater monitoring.", Chemosphere, 2006, p. 1074-1081, 65.

Li, Z. et al. "Low temperature growth of graphene by chemical vapor deposition using solid and liquid carbon sources.", Journal of the American Chemical Society, 2011, p. 3385-3390, 5, 4.

Li, X. et al. "Simultaneous nitrogen-doping and reduction of graphene oxide.", Journal of the American Chemical Society 2009, p. 15939-15944, 131.

Li, G.R. et al. "Carbon nanotubes with titanium nitride as a low-cost counter-electrode material for dye-sensitized solar cells.", Angewandte Chemie, 2010, p. 3653-3656, 49.

Li, X. et al. "Chemically derived, ultrasmooth graphene nanoribbon semiconductors.", Science, 2008,p. 1229-1232, 319, 5867.

Li J. et al. "Carbon Nanotube Nanoelectrode Array for Ultrasensitive DNA Detection.", Nano Letters, 2003, p. 597-602, 3, 5.

Lin, Y.M. et al. "Operation of Graphene Transistors at Gigahertz Frequencies." Nano Letters, 2009, p. 422, 9.

Lu J. et al. "Nanometal-Decorated Exfoliated Graphite Nanoplatelet Based Glucose Biosensors with High Sensitivity and Fast Response. ", ACS Nano, 2008, p. 1825, 2.

Lu, G.H. et al. "Electrostatic-Force-Directed Assembly of Ag Nanocrystals onto Vertically Aligned Carbon Nanotubes.", Journal of Physical Chemistry C, 2007, p. 17919, 11.

Lu, G.H. et al. "Facile, Noncovalent Decoration of Graphene Oxide Sheets with Nanocrystals.", Nano Research, 2009, p. 192-200, 2.

Lu, G.H. et al. "Gas Detection using Low-Temperature Reduced Graphene Oxide Sheets.", Applied Physics Letters, 2009, 93, 3.

Mao, S. et al. "Coating Carbon Nanotubes with Colloidal Nanocrystals by Combining an Electrospray Technique with Directed Assembly using an Electrostatic Field.", Nanotechnology, 2008, 19, 455610.

Mao, S. et al. "Highly Sensitive Protein Sensor Based on Thermally-Reduced Graphene Oxide Field-Effect Transistor.", Nano Research 2011, p. 921-930, 4, 10.

Mao, S. et al. "Specific Biosensing using Carbon nanotubes Functionalized with gold nanoparticle-antibody conjugates.", Carbon, 2010, 48, 479.

Mao, S. et al. "Specific protein detection using thermally reduced graphene oxide sheet decorated with gold nanoparticle-antibody conjugates.", Advanced Materials, 2010, p. 3521-3526, 22.

Mao, S. et al. "Protein viability on Au Nano particles during an Electrospray and Electrostaic-Force-Directed Assembly Process." Journal of Nanomaterials, 2010, 6.

Martinez, M.T. et al. "Label-Free DNA Biosensors Based on Functionalized Carbon Nanotube Field Effect Transistors.", Nano Letters, 2009, p. 530-536, 9, 2.

Meyer, A.K. et al. "The Structure of Suspended Graphene Sheets.", Nature, 2007, 446, 60.

Mohanty, N. et al. "Graphene-Based Single-Bacterium Resolution Biodevice and DNA Transistor: Interfacing Graphene Derivatives with Nanoscale and Microscale Biocomponents.", Nano Letters, 2008, 8, 4469.

Murakami, T. N. et al. "Highly Efficient Dye-Sensitized Solar Cells Based on Carbon Black Counter Electrodes.", Journal of the Electrochemical Society, 2006, p. A2255-A2261, 153, 12.

Muszynski, R. et al. "Decorating graphene sheets with gold nanoparticles.", The journal of Physical Chemistry Letters C, 2008, p. 5263-5266, 112.

Ni, Z.H. et al. "Probing Charged Impurities in Suspended Graphene Using Raman Spectroscopy.", ACS Nano, 2009, 3, 569.

Novoselov, K.S. et al. "Electric Field Effect on Atomically Thin Carbon Films.", Science, 2004, 306, 666.

Ohno, Y. et al. "Electrolyte-Gated Graphene Field-Effect Transistors for Detecting pH and Protein Adsorption.", Nano Letters, 2009, 9, 3318.

Ouyang, Y. J. et al. "Projected performance advantage of multilayer graphene nanoribbons as a transistor channel material." Nano Res., 2010, p. 8-15, 3.

Park, S. et al. "Colloidal Suspensions of Highly Reduced Graphene Oxide in a Wide Variety of Organic Solvents.", Nano Letters, 2009, p. 1593-1597, 9, 4.

Park, S. et al. "Aqueous Suspension and Characterization of Chemically Modified Graphene Sheets.", Chemistry Materials, 2008, 20, 6592.

Park, S. et al. "Chemical Methods for the Production of Graphenes.", Nature Nanotechnologies, 2009, 4, 217.

Patchkovskii, S. et al. "Graphene Nanostructures as Tunable Storage Media for Molecular Hydrogen.", Proceedings in the National Academy of Science, 2005, 102, 10439.

Pereira, A.C. et al. "Amperometric biosensor for lactate based on lactate dehydrogenase and Meldola Blue coimmobilized on multi-wall carbon-nanotube.", Sensor and Actuators B, 2006, p. 269-276, 124.

Petersen, M. et al. "Improving the Efficiency of FP-LAPW Calculations.", Computer Physics Communications, 2000, p. 126-294.

Ponomarenko, L.A. et al. "Chaotic Dirac Billiard in Graphene Quantum Dots.", Science, 2008, 320, 356.

Qazi, M. et al. "Trace Gas Detection using Nanostructured Graphite Layers.", Applied Physics Letters, 2007, 91, 3.

Reina, A. et al. "Growth of large-area single- and bi-layer graphene by controlled carbon precipitation on polycrystalline Ni surfaces.", Nano Research 2009, p. 509-516, 2.

Russell, J. et al. "Configuration-sensitive molecular sensing on doped graphene sheets.", Nano Research, 2010.

Satija, J. et al. "Emerging use of nanostructure films containing capped gold nanoparticles in biosensors.", Nanotechnology, Science and Applications, 2010, p. 171-188, 3.

Schedin, F. et al. "Detection of Individual Gas Molecules Adsorbed on Graphene.", Nature Materials, 2007, 6, 652.

Scherrer, P. et al "Bestimmung der Grosse und der inneren Struktur von Kolloidteilchen mittels Rontgenstrahlen.", Nachr. Ges. Wiss. Gottingen, 1918, p. 98-100, 26.

Shan, C.S. et al. "Graphene/AuNPs/chitosan nanocomposites film for glucose biosensing.", Biosensors and Bioelectronics, 2010, p. 1070-1074, 25.

Shan, C.S. et al. "Direct Electrochemistry of Glucose Oxidase and Biosensing for Glucose Based on Graphene.", Analytical Chemistry, 2009, 81, 2378.

Simonian, A.L. et al. "FET-Based Biosensors for the Direct Detection of Organophosphate Neurotoxins.", Electroanalysis, 2004, p. 1896-1906, 16, 22.

Sofo, J.O. et al. "Graphane: a two-dimensional hydrocarbon.", Physical Review, 2007, 75, 4.

Star, A et al. "Electronic Detection of Specific Protein Binding Using Nanotube FET Devices.", Nano Letters, 2003, p. 459-463, 3, 4.

Thotiyl, M.M. et al. "Pd Supported on Titanium Nitride for Efficient Ethanol Oxidation.", Journal of Physical Chemistry C, 2010, p. 17934-17941, 114.

Wang, D. et al. "Self-assembled TiO-graphene hybrid nanostructures for enhanced Li-Ion insertion.", ACS Nano, 2009, p. 907-914, 3, 4.

Wang, H. et al. "Solvothermal reduction of chemically exfoliated graphene sheets.", Journal of the American Chemical Society, 2009, p. 9910-9911, 131.

Wang, M. et al. "CoS supercedes Pt as efficient electrocatalyst for triodide reduction in dye-sensitized solar cells.", Journal of the American Chemical Society, 2009, p. 15976-15977, 131.

Wang, X.J. et al. "Room-temperature defect-engineered spin filter based on a non-magnetic semiconductor.", Nature Materials, 2009, p. 198-202, 8.

(56) References Cited

OTHER PUBLICATIONS

Wang, S.G. et al. "High Field Emission Reproducibility and Stability of Carbon Nanosheets and Nanosheet-based Backgated Triode Emission Devices.", Applied Physics Letters, 2006, 89, 3.
Wang, X. et al. "Transparent, Conductive Graphene Electrodes for Dye-Sensitized Solar Cells.", Nano Letters, 2008, 8, 323.
Wang, X.R. et al. "N-Doping of Graphene through Electrothermal Reactions with Ammonia.", Science, 2009, 324, 768.
Wang, Y. et al. "Application of Graphene-Modified Electrode for Selective Detection of Dopamine.", Electrochemical Communications, 2009, 11, 889.
Wang, Z. et al. "Laterally confined graphene nanosheets and graphene/Sno2 composites as high-rate anode materials for lithium-ion batteries.", Nano Research, 2010, p. 748-756, 3.
Watcharotone, S. et al. "Graphene-Silica Composite Thin Films as Transparent Conductors.", Nano Letters, 2007, 7, 1888.
Wei, Q. et al. "A novel label-free electrochemical immunosensor based on graphene and thionine nanocomposite.", Sensors and Actuators B: Chemical, 2010, p. 314-318, 149.
Weinert, M. et al. "FLAPW: Applications and Implementations.", Journal of Physics: Condensed Matter, 2009, p. 1-14, 21.
Wen, Z. et al. "Metal nitride.graphene nanohybrids: general synthesis and multifunctional titanium nitride/graphene electrocatalyst.", Advanced Materials, 2011, p. 5445-5450, 23.
Wohlstadter, J.N. et al. "Carbon Nanotube-Based Biosensor.", Advanced Materials, 2003, p. 1184-1187, 15, 14.
Wu, M. et al. "Low-cost molybdenum carbide and tungsten carbide counter electrodes for dye-sensitized solar cells.", Angew. Chemie, 2011, p. 3520-3524, 50.
Wu, G. et al. "High-performance electrocatalysts for oxygen reduction derived from polyaniline, iron, and cobalt.", Science, 2011, p. 443-447, 332.
Wu. H. et al. "Glucose biosensor based on immobilization of glucose oxidase in platinum nanoparticles/graphene/chitosan nanocomposite film.", Talanta, 2009, p. 403-406, 80.
Xu, C. et al. "Deposition of Co3O4 nanoparticles onto exfoliated graphite oxide sheets.", Journal of Materials Chemistry, 2008, p. 5625-5629, 18.
Yang, D. et al. "Chemical Analysis of Graphene Oxide Films after Heat and Chemical Treatments by X-ray Photoelectron and Micro-Raman Spectroscopy.", Carbon, 2009, 47, 145.
Yang, S. et al. "Fabrication of graphene-encapsulated oxide nanoparticles: towards high-performance anode materials for lithium storage.", Angew. Chem. Int. Ed., 2010, p. 8408-8411, 49.
Zhong, Z. et al. "Nanogold-enwrapped graphene naocomposites as trace labels for sensitivity enhancement of electrochemical immunosensors in clinical immunoassays: carcinoembryonic antigen as a model.", Biosensors and Bioelectronics, 2010, p. 2379-2383, 25.
Zhou, M. et al. "Electrochemical Sensing and Biosensing Platform Based on Chemically Reduced Graphene Oxide.", Analytical Chemistry, 2009, 81, 5603.
Aragay, G. et al., "Recent Trends in Macro-, Micro-, and Nanomaterial-Based Tools and Strategies for Heavy-Metal Detection," Chemical reviews (2011) 111, 3433-58.
Avouris, P., "Graphene: Electronic and Photonic Properties and Devices," Nano Lett. (2010) 10, 4285-4294.
Bae, S. Y. et al., "Large-Area Graphene Films by Simple Solution Casting of Edge-Selectively Functionalized Graphite," Acs Nano (2011) 5, 4974-4980.
Bae, S., et al., "Roll-to-Roll Production of 30-Inch Graphene Films for Transparent Electrodes," Nat Nanotechnol (2010) 5, 574-578.
Bahsi, Z. B. et al., "A Novel Label-Free Optical Biosensor Using Synthetic Oligonucleotides from E. coli O157:H7: Elementary Sensitivity Tests," Sensors-Basel (2009) 9, 4890-4900.
Benayad, A. et al., "Controlling Work Function of Reduced Graphite Oxide with Au-Ion Concentration," Chem. Phys. Lett. (2009) 475, 91-95.
Beqa L.et al., "Gold Nanoparticle-Based Simple Colorimetric and Ultrasensitive Dynamic Light Scattering Assay for the Selective Detection of Pb(Ii) from Paints, Plastics, and Water Samples," ACS applied materials & interfaces (2011) 3, 668-673.
Bloxham, M. J. et al, "Determination of Mercury in Filtered Sea-Water by Flow Injection with on-Line Oxidation and Atomic Fluorescence Spectrometric Detection," J. Anal. At. Spectrom (1996) 11, 511-514.
Bolotin, K. I. et al., "Ultrahigh Electron Mobility in Suspended Graphene," Solid State Communications (2008) 146, 351-355.
Boyanov, M. I. et al., "Mechanism of Pb Adsorption to Fatty Acid Langmuir Monolayers Studied by X-Ray Absorption Fine Structure Spectroscopy," The Journal of Physical Chemistry B (2003) 107,9780-9788.
Burg, B. R. et al., "High-Yield Dielectrophoretic Assembly of Two-Dimensional Graphene Nanostructures," Appl. Phys. Lett. (2009) 94.
Chai, F.et al., "Colorimetric Detection of Pb2+ Using Glutathione Functionalized Gold Nanoparticles," ACS applied materials & interfaces (2010) 2, 1466-1470.
Chen, J. L. et al., "A Functionalized Gold Nanoparticles and Rhodamine 6g Based Fluorescent Sensor for High Sensitive and Selective Detection of Mercury (Ii) in Environmental Water Samples," Anal. Chim. Acta (2007) 599, 134-142.
Chen, K. H. et al., "C-Erbb-2 Sensing Using Algan/Gan High Electron Mobility Transistors for Breast Cancer Detection," Appl. Phys. Lett. (2008) 92.
Chen, K. H. et al., "Low Hg(Ii) Ion Concentration Electrical Detection with Algan/Gan High Electron Mobility Transistors," Sens. Actuators B (2008) 134, 386-389.
Cheng, M. S. et al., "Membrane-Based Electrochemical Nanobiosensor for Escherichia coli Detection and Analysis of Cells Viability," Environ. Sci. Technol. (2011) 45, 6453-6459.
Compton, O. C., "Graphene Oxide, Highly Reduced Graphene Oxide, and Graphene: Versatile Building Blocks for Carbon-Based Materials," Small (2010) 6, 711-723.
Costa, H. O. et al., "Is there a relationship between the pH and volume of saliva and esophageal pH-metry results," Dysphagia (2005) 20 (3), 175-181.
Dan, Y. et al., "Intrinsic Response of Graphene Vapor Sensors," Nano Lett (2009) 9, 1472-1475.
Forzani, E. S. et al., "Tuning the Chemical Selectivity of Swnt-Fets for Detection of Heavy-Metal Ions," Small (2006) 2, 1283-1291.
Fowler, J. D. et al., "Hydrogen Detection by Polyaniline Nanofibers on Gold and Platinum Electrodes," The Journal of Physical Chemistry C (2009) 113, 6444-6449.
Fowler, J. D. et al., "Practical Chemical Sensors from Chemically Derived Graphene," ACS Nano (2009) 3, 301-306.
Fratamico, P. M. et al., "Detection of Escherichia coli O157:H7 in Food Using Real-Time Multiplex Pcr Assays Targeting the Stx(1), Stx(2), Wzy(O157), and the Flic(H7) or Eae Genes," Food Anal Method (2010) 3, 330-337.
Gao et al., "Subthreshold Regime Has the Optimal Sensitivity for Nanowire Fet Biosensors," Nano letters (2010) 10, 547-52.
Gasparik, J. et al., "Concentration of Lead, Cadmium, Mercury and Arsenic in Leg Skeletal Muscles of Three Species of Wild Birds," Journal of Environmental Science and Health, Part A (2010) 45, 818-823.
Gilje, S. et al., "A Chemical Route to Graphene for Device Applications," Nano Lett. (2007) 7, 3394-3398.
Gomez-Navarro, C. et al., "Electronic Transport Properties of Individual Chemically Reduced Graphene Oxide Sheets," Nano Lett (2007) 7, 3499-3503.
Gracias, K. S. et al., "A Review of Conventional Detection and Enumeration Methods for Pathogenic Bacteria in Food," Can. J. Microbiol. (2004) 50, 883-890.
Heidelbaugh, J. J. et al., "Magnitude and Economic Effect of Overuse of Antisecretory Therapy in the Ambulatory Care Setting," Am J Manag Care (2010) 16(9), E228-E234.
Hilder, M. et al., "Direct Electro-Deposition of Graphene from Aqueous Suspensions," Phys Chem Chem Phys (2011) 13, 9187-9193.
Ho, T.-Y. et al., "Determination of Trace Metals in Seawater by an Automated Flow Injection Ion Chromatograph Pretreatment System with Icpms," Talanta (2010) 82, 1478-1484.

(56) References Cited

OTHER PUBLICATIONS

Huang, B. et al., "Adsorption of Gas Molecules on Graphene Nanoribbons and Its Implication for Nanoscale Molecule Sensor," J. Phys. Chem. C (2008) 112, 13442-13446.

Huang, C.-C., "Selective Gold-Nanoparticle-Based "Turn-on" Fluorescent Sensors for Detection of Mercury(Ii) in Aqueous Solution," Anal. Chem. (2006) 78, 8332-8338.

Huang, Y. X. et al., "Graphene-Based Biosensors for Detection of Bacteria and Their Metabolic Activities," J. Mater. Chem. (2011) 21, 12358-12362.

Hwang, J., "Transport Properties of a DNA-Conjugated Single-Wall Carbon Nanotube Field-Effect Transistor," Jpn J Appl Phys (2009) 48, 06FD08.

Ishigami, M. et al., "Atomic Structure of Graphene on Sio2," Nano Lett (2007) 7, 1643-1648.

Ishikawa et al, "A Calibration Method for Nanowire Biosensors to Suppress Device-to-Device Variation," ACS Nano (2009) 3, 3969-3976.

Ishikawa, F. N. et al., "Importance of Controlling Nanotube Density for Highly Sensitive and Reliable Biosensors Functional in Physiological Conditions," Acs Nano (2010) 4, 6914-6922.

Kang, B. S. et al., "Electrical Detection of Deoxyribonucleic Acid Hybridization with Algan/Gan High Electron Mobility Transistors," Appl. Phys. Lett. (2006) 89.

Karunasagar, D. et al., "Development of a 'Collect and Punch' Cold Vapour Inductively Coupled Plasma Mass Spectrometric Method for the Direct Determination of Mercury at Nanograms Per Litre Levels," J. Anal. At. Spectrom (1998) 13, 679-682.

Kawasaki, S. et al., "Evaluation of a Multiplex Pcr System for Simultaneous Detection of *Salmonella* Spp., Listeria Monocytogenes, and *Escherichia coli* O157:H7 in Foods and in Food Subjected to Freezing," Foodborne Pathog Dis (2009) 6, 81-89.

Kobayashi, T. et al., "Channel-Length-Dependent Field-Effect Mobility and Carrier Concentration of Reduced Graphene Oxide Thin-Film Transistors," Small (2010) 6, 1210-1215.

Lee, B. Y. et al., "Universal Parameters for Carbon Nanotube Network-Based Sensors: Can Nanotube Sensors Be Reproducible?," Acs Nano (2011) 5, 4373-4379.

Lee, N. J. et al., "The Interlayer Screening Effect of Graphene Sheets Investigated by Kelvin Probe Force Microscopy," Appl. Phys. Lett. (2009) 95.

Leopold, K. et al., "Methods for the Determination and Speciation of Mercury in Natural Waters—a Review," Anal Chim Acta (2010) 663, 127-138.

Li, T. et al., "Lead(Ii)-Induced Allosteric G-Quadruplex Dnazyme as a Colorimetric and Chemiluminescence Sensor for Highly Sensitive and Selective Pb2+ Detection," Analytical chemistry (2010) 82, 1515-1520.

Li, W. W. et al., "Reduced Graphene Oxide Electrically Contacted Graphene Sensor for Highly Sensitive Nitric Oxide Detection," Acs Nano (2011) 5, 6955-6961.

Li, Z. Y. et al., "An Applied Approach in Detecting *E. coli* O157:H7 Using Immunological Method Based on Chemiluminescence and Magnetic Nanoparticles," Acta Chim. Sinica (2010) 68, 251-256.

Liu, J. et al., "Stimuli-Responsive Disassembly of Nanoparticle Aggregates for Light-up Colorimetric Sensing," Journal of the American Chemical Society (2005) 127,12677-12683.

Lu, G. H. et al., "Electrostatic-Force-Directed Assembly of Ag Nanocrystals onto Vertically Aligned Carbon Nanotubes," J. Phys. Chem. C (2007) 111, 17919-17922.

Lu, G. H. et al., "Gas Detection Using Low-Temperature Reduced Graphene Oxide Sheets," Appl. Phys. Lett. (2009) 94, 083111.

Lu, G. H. et al., "Room-Temperature Gas Sensing Based on Electron Transfer between Discrete Tin Oxide Nanocrystals and Multiwalled Carbon Nanotubes," Adv. Mater. (2009) 21, 2487-2491.

Lu, G. H., "Toward Practical Gas Sensing with Highly Reduced Graphene Oxide: A New Signal Processing Method to Circumvent Run-to-Run and Device-to-Device Variations," ACS Nano (2011) 5, 1154-1164.

Luo, L. B. et al, "Silicon Nanowire Sensors for Hg2+ and Cd2+ Ions," Appl. Phys. Lett. (2009) 94, 193101.

Mahajan, R. K. et al., "A Mercury(Ii) Ion-Selective Electrode Based on Neutral Salicylaldehyde Thiosemicarbazone," Talanta (2003) 59, 101-105.

Majid, E. et al., "Boron Doped Diamond Biosensor for Detection of *Escherichia coli*," J. Agric. Food Chem. (2008) 56, 7691-7695.

Marcano, D. C. et al., "Improved Synthesis of Graphene Oxide," Acs Nano (2010) 4, 4806-4814.

McAllister, M. J. et al., "Single Sheet Functionalized Graphene by Oxidation and Thermal Expansion of Graphite," Chem. Mater. (2007) 19, 4396-4404.

Mohamed Ali, E. et al., "Ultrasensitive Pb2+ Detection by Glutathione-Capped Quantum Dots," Analytical chemistry (2007) 79, 9452-9458.

Morton J. et al., "Detection of Trace Heavy Metal Ions Using Carbon Nanotube-Modified Electrodes," Electroanalysis (2009) 21, 1597-1603.

Pavlish, J. H. et al., "State Review of Mercury Control Options for Coal-Fired Power Plants. Fuel Process," Technol (2003) 82, 89-165.

Puk, R. et al., "Determination of Mercury (Ii), Monomethylmercury Cation, Dimethylmercury and Diethylmercury by Hydride Generation, Cryogenic Trapping and Atomic-Absorption Spectrometric Detection," Anal. Chim. Acta (1994) 292, 175-183.

Quinlin, R. A. et al., "Transfer of Carbon Nanosheet Films to Nongrowth," Zero Thermal Budget Substrates. J Vac Sci Technol B (2011) 29, 030602.

Rao, C. N. et al, "Graphene: The New Two-Dimensional Nanomaterial," Angew Chem Int Ed Engl (2009) 48, 7752-77.

Richardson, S. D. et al., "Water Analysis: Emerging Contaminants and Current Issues," Anal. Chem. (2011) 83, 4614-4648.

Robinson, J. T. et al., "Wafer-Scale Reduced Graphene Oxide Films for Nanomechanical Devices," Nano letters (2008) 8, 3441-3445.

Sen, K. et al., "Development of a Sensitive Detection Method for Stressed *E. coli* O157:H7 in Source and Finished Drinking Water by Culture-Qpcr," Environ. Sci. Technol. (2011) 45, 2250-2256.

Shukla, G. S. et al., "The Present Status of Biological Effects of Toxic Metals in the Environment: Lead, Cadmium, and Manganese," Canadian Journal of Physiology and Pharmacology (1984) 62, 1015-1031.

Singh, A. K. et al., "Gold Nanorod Based Selective Identification of *Escherichia coli* Bacteria Using Two-Photon Rayleigh Scattering Spectroscopy," Acs Nano (2009) 3, 1906-1912.

Singh, J. et al, "A Scorpion Probe-Based Real-Time Pcr Assay for Detection of *E-coli* O157:H7 in Dairy Products," Foodborne Pathog Dis (2009) 6, 395-400.

Singh, J. et al., "A Molecular Beacon-Based Duplex Real-Time Polymerase Chain Reaction Assay for Simultaneous Detection of *Escherichia coli* O157:H7 and Listeria Monocytogenes in Milk and Milk Products," Foodborne Pathog Dis (2009) 6, 1195-1201.

Stankovich, S. et al., "Stable Aqueous Dispersions of Graphitic Nanoplatelets Via the Reduction of Exfoliated Graphite Oxide in the Presence of Poly (Sodium 4-Styrenesulfonate)," J. Mater. Chem. (2006) 16, 155-158.

Sudibya, H. G. et al, "Electrical Detection of Metal Ions Using Field-Effect Transistors Based on Micropatterned Reduced Graphene Oxide Films," Acs Nano (2011) 5, 1990-1994.

Sun, D. F. et al., "High Performance Supercapacitor Electrode Based on Graphene Paper Via Flame-Induced Reduction of Graphene Oxide Paper.," J. Power Sources (2013) 222, 52-58.

Swearingen, C. B. et al., "Immobilization of a Catalytic DNA Molecular Beacon on Au for Pb(Ii) Detection," Analytical chemistry (2004) 77, 442-448.

Bin, W. et el, "High Yield Production of Graphene and Its Improved Property in Detecting Heavy Metal Ions," New Carbon Materials (2011) 26, 31-35.

Wu, Q. Z. et al., "Biomolecule-Assisted Synthesis of Water-Soluble Silver Nanoparticles and Their Biomedical Applications," Inorg Chem (2008) 47, 5882-5888.

(56) References Cited

OTHER PUBLICATIONS

Xia, F. N. et al., "Graphene Field-Effect Transistors with High on/Off Current Ratio and Large Transport Band Gap at Room Temperature," Nano Lett. (2010) 10, 715-718.
Zahir, F. et al., "Low Dose Mercury Toxicity and Human Health." Environ. Toxicol, Pharmacol (2005) 20, 351-360.
Zeng, S. W. et al., "A Review on Functionalized Gold Nanoparticles for Biosensing Applications," Plasmonics (2011) 6, 491-506.
Zhang, T., "Self-Assembled 1-Octadecanethiol Monolayers on Graphene for Mercury Detection," Nano Lett (2010) 10, 4738-4741.
Zhao, X.-H. et al., "Graphene-Dnazyme Based Biosensor for Amplified Fluorescence "Turn-on" Detection of Pb2+ with a High Selectivity," Analytical chemistry (2011) 83, 5062-5066.
Zhou, J. Y. et al, "Novel in-Situ Decoration of Single-Walled Carbon Nanotube Transistors with Metal Nanoparticles," J Nanosci Nanotechnol (2010) 10, 3890-3894.
Zhu, Y. et al., "Graphene and Graphene Oxide: Synthesis, Properties, and Applications," Adv. Mater (2010) 22, 3906-3924.
PCT/US2015/043449 International Search Report and Written Opinion dated Oct. 28, 2015 (10 pages).

\* cited by examiner

GRAPHENE-BASED FIELD-EFFECT TRANSISTOR BIOSENSORS

CROSS REFERENCE TO RELATED APPLICATIONS

This application claims priority to U.S. Provisional Patent Application Ser. No. 61/444,395, filed Feb. 18, 2011, and which is incorporated by reference herein in its entirety.

STATEMENT REGARDING FEDERALLY SPONSORED RESEARCH

This invention was made with government support under CMMI-0900509, CBET-0803142, and ECCS-0708998 awarded by the National Science Foundation and DE-EE003208 awarded by the Department of Energy. The United States government has certain rights in the invention.

INTRODUCTION

In general, FET-based biosensors are devices that respond to changes in its' biological environment and converts this response into a signal that can be read. FET-based biosensors have been used to detect biomolecules, such as DNA and single-bacterium, and biological conditions, such as pH. The detection of biomolecules in a sample provides valuable information for research and commercial applications, such as biomedical diagnostics, drug screening, monitoring of environmental contamination or food safety evaluation, and drugs discovery applications. There is a need for graphene-based field-effect transistor (FET)-based biosensors for the detection of biomolecules.

SUMMARY

In an aspect, the disclosure provides a field-effect transistor-based biosensor including a nanostructure, one or more nanoparticles in contact with the nanostructure and one or more biomolecules in contact with the one or more nanoparticles. The nanostructure includes a graphene sheet, a graphene oxide sheet or a hybrid thereof.

In another aspect, the disclosure provides a method of detecting a target biomolecule in a sample. The method includes contacting said field-effect transistor-based biosensor with a sample containing or suspected of containing the target biomolecule and monitoring a change in the electrical characteristic.

In another aspect, the disclosure provides a method of making said field-effect transistor-based biosensor. The one or more nanoparticles are deposited onto the nanostructure by electrospray and electrostatic force directed assembly or by drop-casting.

Other aspects of the invention will become apparent by consideration of the detailed description and accompanying drawings.

BRIEF DESCRIPTION OF THE DRAWINGS

FIG. 2(c) shows an atomic force microscope (AFM) image (non-contact mode) of the as-fabricated FET device. FIG. 2(d) shows the height profiles from the AFM image (1) across a TRGO sheet on the Au electrode; (2) across the edge of a TRGO sheet and (3) across Au NP-antibody conjugates on a TRGO sheet (the line 3 is purposely moved slightly to the right from the original scanning line to show the Au NP).

FIG. 3(c) shows the Raman spectra of GO before and after the thermal treatment showing changes in the D (1340 cm$^{-1}$), G (1580 cm$^{-1}$) and 2D (2670 cm$^{-1}$) bands. The ratio of $I_{2D}/I_G$ decreased from 0.15 to 0.06 after the thermal treatment, which is indicative of the reduction of the GO sheet. The same thermal treatment was performed to all of the sensors (more than 30) and it was found that the thermal treatment could reduce the GO device resistance to a similar level, which confirmed the repeatability of the thermal treatment and the device fabrication.

DETAILED DESCRIPTION

Figure 1:
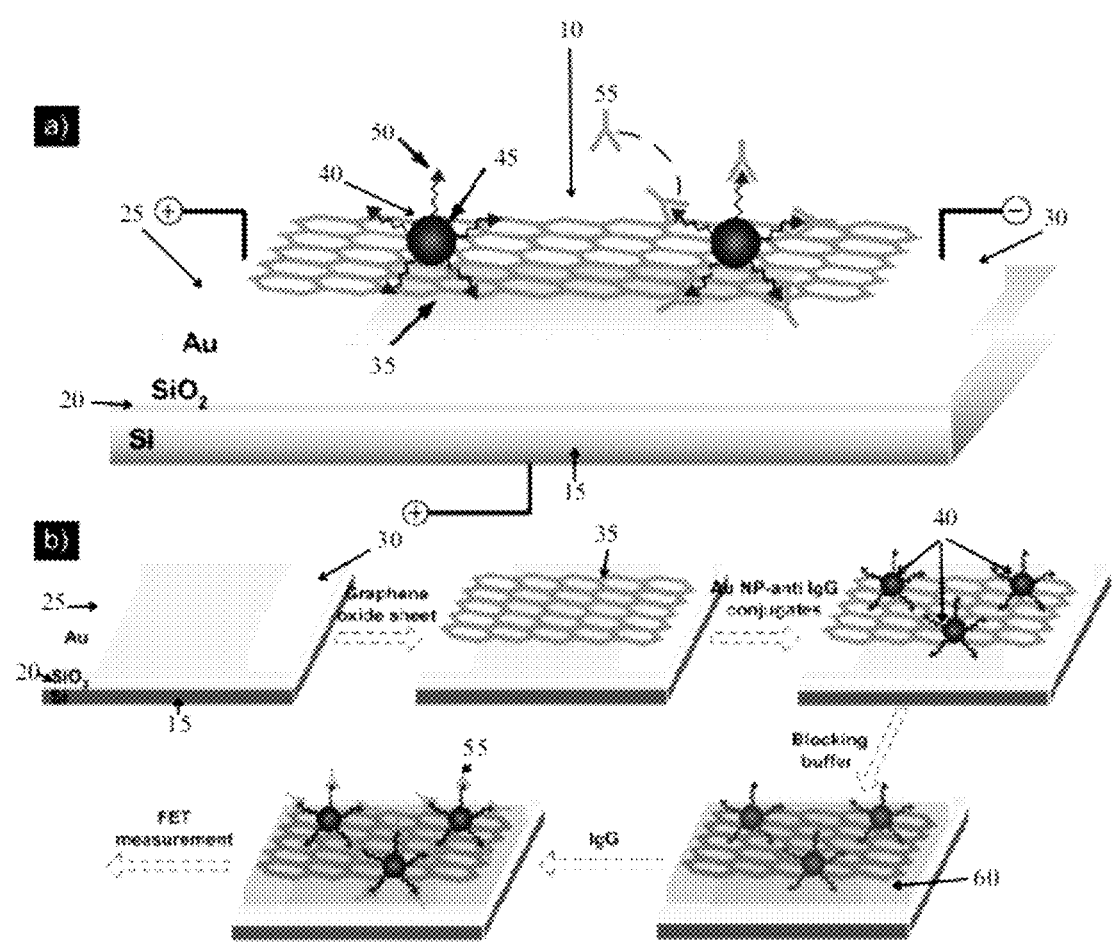
FIG. 1(a) shows a schematic of a thermally-reduced graphene oxide (TRGO) FET. Anti-IgG is anchored to the TRGO sheet surface through gold (Au) nanoparticles (NPs) and functions as a specific recognition group for the IgG binding. The electrical detection of protein binding (IgG to anti-IgG) is accomplished by FET and direct current (dc) measurements.
FIG. 1(b) shows a schematic illustration of the TRGO FET fabrication process. TRGO sheets were firstly dispersed on the electrodes and then decorated with Au NP-antibody conjugates through noncovalent attachment.

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass both direct and indirect mountings, connections, supports, and couplings. Further, "connected" and "coupled" are not restricted to physical or mechanical connections or couplings.

Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

It also is understood that any numerical range recited herein includes all values from the lower value to the upper value. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this application.

Further, no admission is made that any reference, including any patent or patent document, cited in this specification constitutes prior art. In particular, it will be understood that, unless otherwise stated, reference to any document herein does not constitute an admission that any of these documents forms part of the common general knowledge in the art in the United States or in any other country. Any discussion of the references states what their authors assert, and the applicant reserves the right to challenge the accuracy and pertinency of any of the documents cited herein Electrical detection of biomolecules using nanomaterials can often achieve high sensitivity because nanomaterials are extremely sensitive to electronic perturbations in the surrounding environment. Carbon nanotubes (CNT) and CNT-based field-effect transistor (FETs) biosensors have been used for the detection of protein binding and DNA hybridization events. Although CNT-based FETs are promising candidates for biosensors with high sensitivity, the device sensitivity is still limited by surface area and electrical properties of CNTs. CNTs as produced consist of both semiconducting and metallic tubes and there are no available methods for producing pure semiconducting or metallic tubes. The variations in the tube properties lead to devices with varying characteristics and performance, which is an obstacle to CNT-based FET reliability.

Graphene, a single layer of carbon atoms in a two-dimensional honeycomb lattice, has potential applications in the electrical detection of biological species due to their unique physical properties. Graphene-based sheets are flat and large in lateral dimensions, which make it easier for device fabrication (e.g., making electrical contact with electrodes). Compared to CNTs, graphene-based sheets have a higher carrier mobility and specific surface area, which enhances the sensor performance. The use of graphene has been explored for various applications. For example, large-sized graphene film FETs were fabricated for the electrical detection of DNA hybridization; graphene oxide (GO) was used in single-bacterium and label-free DNA sensors, and electrolyte-gated graphene FETs was used for electrical detection of pH. Despite the sparse demonstration of graphene for biosensing applications, graphene-based FETs have not been reported for detection of protein binding (e.g., antibody to antigen) events. Methods of directly immobilizing proteins onto CNTs or graphene oxide have been shown to be unstable and the attached proteins can be readily removed through simple washing processes that are frequently used during the biosensor fabrication. This introduces undesirable effects such as poor device reliability/repeatability and non-specificity of the sensor.

Graphene oxide (GO) is a graphene-based material which can be mass-produced at a lower cost compared to pure graphene. GO can be synthesized in large quantities by oxidizing inexpensive graphite powders using strong oxidants. While unreduced GO is insulating, reducing the GO partially allows the GO to be more conductive. However, the electronic properties of reduced GO are not as good as those of pure graphene. GO can also be reduced through different methods with tailored properties by controlling the reduction conditions. The use of metal nitride/graphene nanohybrid sheets may also provide a highly efficient, low-cost, specific electrocatalyst that may be used as the conducting channel in the FET-based biosensor.

The present disclosure relates to a field-effect transistor (FET)-base biosensor and uses thereof, and in particular, to FET-based biosensors using graphene-based sheets decorated with nanoparticle-biomolecule conjugates. The present disclosure also relates to FET-based biosensors using metal nitride/graphene hybrid sheets. Because the carrier mobility and the specific surface area of a thin graphene sheet are larger than those of CNTs, graphene-based FET-based biosensors may have comparable or better sensing performance than CNT-based FET-based biosensors. The disclosed reduced GO sheet FET-based biosensor proves to be surprisingly excellent at detecting biomolecules, despite the fact that the electronic properties of reduced GO are not as good as those of pure graphene.

The present disclosure provides a reliable method to immobilize biomolecules (e.g., antibodies or the like) in graphene-based biosensors and a methodology for avoiding nonspecific protein immobilization on graphene-based sheets and providing at the same time a stable binding for protein probes through robust nanoparticles. The immobilization of the biomolecules via the nanoparticles allows for a more stable attachment of the biomolecules to the nanostructure. The more stable attachment provides improved device reliability/repeatability and improved specificity of the sensor. The disclosure provides a methodology for avoiding nonspecific protein immobilization on graphene-based sheets and providing a stable binding for biomolecules through robust nanoparticles.

Referring to FIG. 1a, a FET-based biosensor 10 includes a substrate 15 having a passivation layer 20, a source electrode 25 and a drain electrode 30 each disposed on one surface of the substrate, and a nanostructure or graphene-based sheet 35 configured to be a conducting channel suspended above the substrate and to electrically connect the source 25 and drain 30 electrodes. The graphene-based sheet 35 is decorated with nanoparticle-biomolecule conjugates 40, which anchor biomolecules 50 to the surface of the nanostructure or graphene-based sheet 35 through nanoparticles 45. The nanoparticle-biomolecule conjugate 40 may include gold nanoparticles labeled or conjugated with anti-immunoglobulin G (anti-IgG). The anti-IgG antibody functions as the specific recognition group for the target biomolecule 55, i.e., an IgG antibody.

In some embodiments, the nanostructure or graphene-based sheet may include a graphene sheet, a graphene oxide sheet, or a hybrid sheet thereof. Examples of graphene-based sheets include, but are not limited to, thermally-reduced graphene oxide, chemically-reduced graphene oxide, doped-graphene, doped-graphene oxide, doped-reduced graphene oxide, and metal nitride/graphene nanohybrid. Examples of metal nitride/graphene nanohybrid include metal nitride/nitrogen-doped graphene. A metal nitride includes any metal or metalloid which forms a compound with nitrogen. A metal nitride may include a transition metal nitride or a post-transition metal nitride. In certain embodiments, the metal nitrides comprise titanium nitride, tantalum oxynitride or gallium nitride. The metal nitride/graphene nanohybrid may comprise titanium nitride/nitrogen-doped graphene.

In some embodiments, the nanoparticle may include a metal, a metal oxide, or a metal nitride. In some embodiments, the nanoparticle may include a noble metal or a noble metal oxide. For example, the nanoparticle may include ruthenium, rhodium, palladium, silver, osmium, iridium, platinum, gold, mercury, rhenium, titanium, niobium, and tantalum. In certain embodiments, the nanoparticle comprises gold or silver.

In some embodiments, the biomolecule conjugated to the nanoparticle may include a protein, nucleic acid molecule, microorganism, and a low molecular weight organic compound. Examples include, but are not limited to, an immune protein, an antigen, an enzyme, a nonimmune protein, an immunoglobulin-binding protein, a sugar-binding protein, a sugar chain recognizing sugar, fatty acid or fatty acid ester, a ligand, an aptamer, and polypeptide or oligopeptide having ligand-binding ability. Examples of an immune protein may include an antibody whose antigen is a target biomolecule, and a hapten. Examples of such an antibody may include various immunoglobulins such as IgG, IgM, IgA, IgE or IgD. A particular example includes an anti-IgG antibody conjugated to the nanoparticle which can be used to detect the target biomolecule IgG.

An enzyme used to conjugate a nanoparticle may include any enzyme that exhibits an activity to a target biomolecule metabolized by the enzyme. Examples of an enzyme include oxidoreductases, hydrolases, isomerases, lyases and synthetases. For example, when the target biomolecule is lactate or NADH, a lactate dehydrogenase may be conjugated to the nanoparticle. When the target biomolecule is glucose or cholesterol, glucose oxidase or cholesterol oxidase, respectively may be conjugated to the nanoparticle. When the target biomolecule is an agricultural chemical, pesticide, narcotic drug, cocaine, heroin, crack or the like, enzymes that show specific reaction with a substrate metabolized from the aforementioned target biomolecules may be used such as acetylcholine esterase, catecholamine esterase, noradrenalin esterase or dopamine esterase. A particular example includes lactate dehydrogenase.

Various microorganisms, such as *Escherichia coli*, may be used as a biomolecule. A nucleic acid molecule may include DNA or RNA, including native DNA and RNA, recombinant DNA and RNA produced by gene recombination and chemically synthesized DNA and RNA. A low molecular weight organic compound may include any given compound that can be synthesized by a common method of synthesizing an organic compound. Examples of nonimmune protein include avidin (streptoavidin), biotin, and a receptor. An immunoglobulin-binding protein may include protein A, protein G, and a rheumatoid factor. An example of a sugar-binding protein includes lectin. Examples of fatty acid or fatty acid ester include stearic acid, arachidic acid, behenic acid, ethyl stearate, ethyl arachidate, and ethyl behenate.

The biomolecule may be conjugated to the nanoparticle using methods known in the art. For example, stable gold nanoparticle protein conjugates can be prepared by passive adsorption due to electrostatic and hydrophobic interactions between the protein and the surface layer of the colloidal gold. Conjugation methods also include chemical complexing, which may be either ionic or non-ionic in nature, or covalent binding. An example of chemical complexing method is disclosed in U.S. Pat. No. 5,521,289, which describes reducing a gold salt in an organic solvent containing a triarylphosphine or mercapto-alkyl derivative bearing a reactive substituent, X, to give small nanoparticles carrying X substituents on linkers bound to the surface through Au—P or Au—S bonds. The colloidal solution is treated with a protein bearing a substituent Y that reacts with X to link the protein covalently to the nanoparticle. An example of binding oligonucleotides to nanoparticles is disclosed in U.S. Pat. No. 7,208,587, which describes attaching oligonucleotides to nanoparticles by means of a linker comprising a cyclic disulfide. Biomolecules conjugated to nanoparticles are commercially available. Examples include gold nanoparticles labeled with anti-immunoglobulin G.

In some embodiments, the nanoparticle-biomolecule conjugate is decorated onto the nanostructure using an electrospray and electrostatic force directed assembly method or a drop-casting method. An example of an electrospray and electrostatic force directed assembly method is disclosed in Mao et al., Nanotechnology (2008) 19:455610, which describes decorating carbon nanotubes with nanocrystals using a combination of an electrospray technique, which creates a high level of electrical charge on the electrosprayed aerosol nanocrystals, with directed assembly using an electrostatic field. In a drop-casting method, a nanoparticle-biomolecule conjugate solution is dropped onto the nanostructure and allowed to dry. Various factors and conditions may influence the drop-cast procedure such as the liquid amount, liquid viscosity, liquid evaporation rates, drop height, drop angle, drop atmosphere, drop splash, the dropping device and the desired depth or height, width, configuration and other dimensions of the nanostructure to be decorated.

Using these non-chemical methods, the nanoparticle, and hence the nanoparticle-biomolecule conjugate, is attached to the nanostructure using non-covalent bonding, such as hydrogen bonds, electrostatic bonds, van der Waals forces, and hydrophobic bonds. The nanoparticles and hence the nanoparticle-biomolecule conjugates may be attached to the nanostructure by van der Waals forces. The non-covalent attachment of the nanoparticle to the nanostructure avoids the effect of changing the electrical characteristics of the nanostructure or graphene-based sheet that may occur with a covalent bond, such as when wet-chemistry strategies are used to assemble nanoparticles onto nanostructures.

In some embodiments, the source and drain electrodes may be formed of any material having electrical conductivity. Examples include, but are not limited to, gold (Au), platinum (Pt) or palladium (Pd). In some embodiments, the substrate may include silicon, silicon dioxide, aluminum oxide, sapphire, germanium, gallium arsenide an alloy of silicon and germanium or indium phosphide. An example of a substrate includes a Si wafer. In some embodiments, the passivation layer may include aluminum, zinc, titanium, silicon, or an oxide or nitride thereof, or a synthetic resin such as, but are not limited to, polymethyl methacrylate, polyester, polystyrene, polyethylene terephthalate, polycarbonate, polyvinylidene chloride or triacetate. An example of a passivation layer includes $SiO_2$.

Referring to FIG. 1b, the method of detecting a target biomolecule in a sample includes contacting the FET-based biosensor with a sample containing or suspected of containing the target biomolecule and monitoring a change in an electrical characteristic. The method of detecting the target biomolecule involves measuring an electrical signal generated by the conversion of the biomolecular interaction between the target biomolecule and the biomolecule of the nanoparticle-biomolecule conjugate into corresponding output information and/or signals. In some embodiments, the biomolecular interaction may include a protein-protein interaction, a protein-oligonucleotide interaction or a protein-based interaction. Examples of protein-protein interaction include antigen-antibody, receptor-ligand, enzyme/substrate, enzyme/coenzyme, enzyme/activator, and enzyme/inhibitor binding.

In some embodiments, a FET-based biosensor including a nanoparticle-antibody conjugate may be used to detect an antigen. The method may include a blocking buffer (BB) to prevent possible nonspecific binding events. The FET-based biosensor may be incubated with the BB prior to testing of a sample with the FET-based biosensor. Prior to adding the sample, the BB is washed off the FET-based biosensor.

After the introduction of target biomolecule, the target biomolecule interacts with the biomolecule of the nanoparticle-biomolecule conjugate and induces significant changes in the electrical characteristics of the FET-based biosensor device, which would be investigated by FET and direct current (dc) measurements. In some embodiments, the change in an electrical characteristic as a function of time indicates the presence of the target biomolecule. In some embodiments, the electrical characteristic may include conductance, capacitance, potential, resistance and inductance.

In some embodiments, the binding event between the biomolecule and the target biomolecule would induce an increase in the electrical signal. In some embodiments, the electrical signal would increase at least 0.001%, 0.01%, 0.1%, 1%, 10%, 20%, 50%, 70% or more, compared to the electrical signal before the sample was added to the FET-based biosensor or compared to the electrical signal of a control sample. In some embodiments, the binding event between the biomolecule and the target biomolecule would induce a decrease in the electrical signal. In some embodiments, the electrical signal would decrease at least 0.001%, 0.01%, 0.1%, 1%, 10%, 20%, 50%, 70% or more, compared to the electrical signal before the sample was added to the FET-based biosensor or compared to the electrical signal of a control sample. A control sample may include a similar composition to the tested sample but without any target biomolecule or alternatively, may contain a known quantity of the target biomolecule.

In an aspect, the method of detecting the target biomolecule may be used for drug screening, drug discovery applications, diagnosis of disease, monitoring of environmental contamination or food safety evaluation. The target biomolecule may be of any origin, including animal, plant or microbiological (e.g., viral, prokaryotic, and eukaryotic organisms, including bacterial, protozoal, and fungal, etc.) depending on the particular purpose of the test. The target biomolecule may include a protein, a nucleic acid, a cell, a microorganism, and a low molecular weight organic compound. Examples of target biomolecules include a coenzyme, bacteria, a fungus, a virus, lactate, NADH, a sugar, including glucose, fatty acids or fatty acid esters, a ligand, an aptamer, a polypeptide or oligopeptide having ligand-binding ability, an antibody, cholesterol, DNA, RNA, an agricultural chemical, pesticide, antibiotic, narcotic drug, cocaine, heroin, crack or the like. In another aspect, the target biomolecule may be an ion such that the pH of the sample may be determined.

In some embodiments, the disclosed FET-based biosensors may be used to detect bacteria and eucarya in food, beverages, water, pharmaceutical products, personal care products, dairy products or environmental samples. The disclosed FET-based biosensors are also useful for the analysis of raw materials, equipment, products or processes used to manufacture or store food, beverages, water, pharmaceutical products, personal care products, dairy products or environmental samples.

Alternatively, the disclosed FET-based biosensors may be used to diagnose a condition of medical interest. In some embodiments, the disclosed FET-based biosensors may be used to analyze clinical specimens or equipment, fixtures or products used to treat humans or animals. In some embodiments, the disclosed FET-based biosensors may be used to detect a target sequence which is specific for a genetically based disease or is specific for a predisposition to a genetically based disease. Non-limiting examples of diseases include, beta-thalassemia, sickle cell anemia, Factor-V Leiden, cystic fibrosis and cancer related targets such as p53, p 10, BRC-1 and BRC-2. In some embodiments, the target sequence may be related to a chromosomal DNA, wherein the detection, identification or quantitation of the target sequence can be used in relation to forensic techniques such as prenatal screening, paternity testing, identity confirmation or crime investigation.

In some embodiments, the disclosed methods of detecting a target biomolecule may include the analysis or manipulation of plants and genetic materials derived there from as well as bio-warfare reagents. The disclosed FET-based biosensors will also be useful in diagnostic applications, in screening compounds for leads which might exhibit therapeutic utility (e.g. drug development) or in screening samples for factors useful in monitoring patients for susceptibility to adverse drug interactions (e.g. pharmacogenomics).

In some embodiments, the method may be used to detect a target biomolecule in a gas sample and/or a liquid sample. To detect the target biomolecule, the FET-based biosensor is exposed to a sample containing or suspected of containing the target biomolecule. In some embodiments, samples include samples used for medical diagnostics, samples used for genetic test, environmental samples, cell culture samples, bacterial cultures, soil samples, food samples, dental samples and veterinary samples. Liquid samples include water and biofluids. Biofluids include, but are not limited to, urine, sweat, breast milk, bile, blood, sputum, semen, cerebrospinal fluid, blister fluid and cyst fluid. The sample may be processed or purified prior to exposure to the FET-based biosensor in accordance with techniques known or apparent to those skilled in the art.

EXAMPLES

Example 1

Experimental Procedure

Materials:

Au nanoparticles labeled with anti-immunoglobulin G (anti-IgG) (10 nm and 20 nm colloidal gold coated with Goat anti-Human IgG (H+L)), Tween 20 and cold water fish gelatin were ordered from Tedpella. IgG from human serum, IgM from human serum, and horseradish peroxidase (HRP) were ordered from Sigma-Aldrich. Bovine serum albumin (BSA) was purchased from Rockland. Phosphate buffered saline (PBS) (pH 7.4, ×1) (Fisher BioReagents) was used as the solvent for IgG, HRP, IgM, and the blocking buffer (BB). All solutions were used without further purification and prepared with distilled and deionized water (Cellgro).

Preparation of TRGO FET:

Gold interdigitated electrodes with both finger width and inter-finger spacing (source and drain separation) of about 1 μm and thickness of 50 nm were fabricated using an e-beam lithography process (Raith 150 lithography tool, 30 kV) on an Si wafer with a top layer of thermally-formed $SiO_2$ (thickness of 200 nm). GO sheets were synthesized from purified natural graphite by a modified Hummers method and fully exfoliated individual GO sheets in water was prepared with the aid of ultrasonication (Park et al., Chem. Mat. (2008) 20:6592; Park et al., Nat. Nanotechnol. (2009) 4:217). To place GO sheets between electrodes, one droplet (0.02 mL) of the GO suspension (0.6 mg GO/mL) was pipetted onto the electrodes and dried under room temperature. The distance between the GO sheet and the $SiO_2$ surface was around 50 nm. The device was then annealed in argon flow (1 L/min) for 1 hr at 200° C. to reduce the GO sheet, remove residue solvents, and improve the contact between the GO sheet and electrodes.

Drop Casting.

The Au NP-antibody conjugates were assembled onto the surface of TRGO sheets by putting a droplet of Au NP-antibody conjugate colloidal solution on the TRGO and incubated for 1 hr. The TRGO base resistance was controlled by adjusting the concentration of the GO solution. The antibody areal density was controlled by tuning the Au NP size (10-20 nm) and the concentration of the Au NP-antibody colloidal solution ($2 \times 10^{12}$ to $1.7 \times 10^{13}$ NPs/mL).

Electrospray and Electrostatic Force Directed Assembly.

Au NP-antibody conjugates were aerosolized by an electrospray process. The conjugates were assembled onto the TRGO sheets by electrostatic force directed assembly (ESFDA). A commercial electrospray aerosol generator ("EAG", TSI Model 3480) was used to spray colloidal Au NP-antibody conjugates. The colloidal conjugates applied with a high dc voltage were extracted through a capillary tube due to the capillary effect and the capillary inlet/outlet pressure difference. The conjugates ejected from the capillary were atomized to form charged fine droplets due to the electrohydrodynamic break-up. Charged Au NP-antibody conjugates were obtained after the solvent evaporation and subsequently assembled onto the surface of TRGO sheets in an electric field. Since the electric field near the TRGO sheets was significantly enhanced due to their small diameters, the charged conjugates were attracted to the external surface of the TRGO sheets via electrostatic force. The assembly time was on the order of hours.

Biosensing:

Before introducing target protein IgG, the devices were modified with a BB (0.1% Tween 20, 0.1% fish gelatin and 1% BSA) to reduce the possible nonspecific binding of IgGs to TRGO sheets and electrodes. Devices were incubated with BB for 2 hrs at room temperature and then washed with the PBS buffer. After that, 0.02 mL IgG sample (2 ng/mL-2 mg/mL) was pipetted onto the device for protein binding for 1 hr, followed by washing and drying. The full protein sensing procedure was performed in ambient environment (i.e., under atmosphere pressure, in air, and at room temperature). The sensor repeatability was studied by using 3-4 sensors in each sensing test, which confirmed that our sensor responses were reproducible. The uncertainty of the sensor response was obtained from the forward and backward FET measurements.

Characterization:

A Hitachi S-4800 UHR FE-SEM instrument was used for scanning electron microscopy (SEM) characterization of the device at an acceleration voltage of 10 kV or 30 kV. Atomic force microscopy (AFM) was conducted with an Agilent Technology 5420 AFM with a cantilever (Nanosensors PPP-NCH). Raman spectroscopy was conducted using a TRIAX 320 spectrometer with a 532 nm laser source. FET and direct current measurements were carried out using a Keithley 2602 SourceMeter. During each step of the sensor fabrication and sensing, the FET measurement was performed by recording the drain current response when ramping the gate voltage $V_g$ from −40.0 to +40.0 V (with a step of 0.1 V), which was directly applied to the back silicon wafer. For the direct current measurement, the drain current was recorded when ramping the drain-source voltage from −2.0 to +2.0 V, while no gate bias was applied.

Example 2

Scanning Electron Microscopy Analysis

Figure 2:
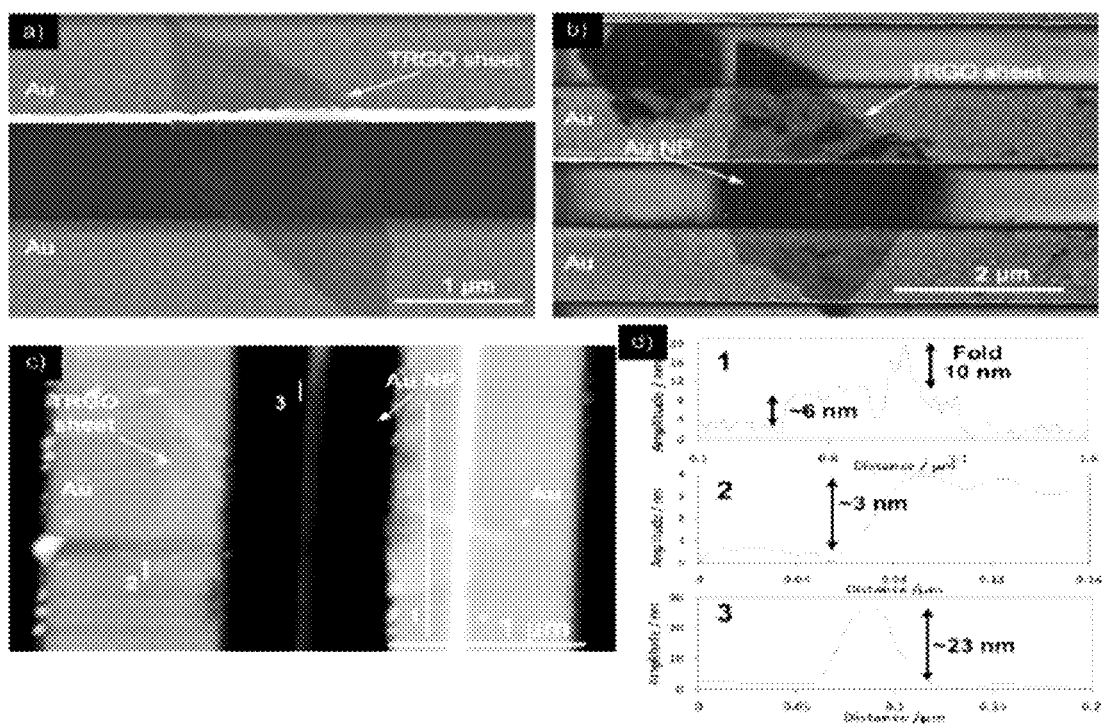
FIG. 2 shows scanning electron microscope (SEM) images of (a) a TRGO sheet and (b) a TRGO sheet decorated with Au NP-antibody conjugates spanning across Au electrodes.

FIGS. 2 (a) and (b) show the scanning electron microscopy (SEM) images of a single TRGO sheet spanning across a pair of Au electrodes before and after the assembly of Au NP-antibody conjugates. Au NPs were seen uniformly distributed on the surface of the TRGO sheet without agglomeration (FIG. 2(b). The probe proteins were covalently bonded to Au NPs (Wohlstadter et al., Adv. Mater. (2003) 15:1184) that were anchored noncovalently to TRGO. The van der Waals binding between Au NPs and graphene may be strong enough to hold the Au NPs with similar sizes in place. The platform successfully survived several cycles of washing and drying as evidenced by SEM images. The atomic force microscopy (AFM) image in FIG. 2(c) shows further details about the device structure. The TRGO sheet had a lateral size of several microns with the presence of wrinkles, folds, and multilevel layering structure. Three height profiles were taken to probe TRGO and NP properties (FIG. 2(d)). Based on the imaging, the thickness of the TRGO sheet was measured as 3-6 nm, which suggests that the TRGO sheet had a few layers. The size of the Au NP-antibody conjugates was measured as approximately 23 nm, which was slightly larger than the pristine Au NP (20 nm). This height difference suggests the presence of antibodies on the Au NP surface. Since the electrospray occurred at room temperature, the anti-IgG on the Au NP surface did not denaturize during the assembly process. The activity of antibodies was preserved during the similar assembly process, which was confirmed by the sensing results presented below.

A specific protein detection biosensor using TRGO sheets decorated with Au NP-antibody conjugates was demonstrated. Anti-Immunoglobulin G (anti-IgG) was anchored to the TRGO surface through Au NPs and functioned as the specific recognition group for the IgG binding. The sensor fabrication process is illustrated in FIG. 1b. The Au NP-antibody conjugates were assembled onto the surface of TRGO sheets by a simple method that combines electrospray with electrostatic force directed assembly (Mao et al., Nanotechnology (2008) 19:455610). A blocking buffer (BB) was used to prevent possible nonspecific binding events. After the introduction of target proteins (IgGs), the protein binding events induced changes in the electrical characteristics of the device, which were investigated by FET and direct current (dc) measurements. This biosensor had a detection limit of 2 ng/mL (~13 pM), which is among the best of carbon nanomaterial (e.g., CNT, graphene, GO)-based protein sensors. The sensor also showed negligible responses to mismatched proteins such as Immunoglobulin M (IgM) and horseradish peroxidase (HRP), which indicates its specificity (data not shown).

The response from the sensor increased with the increase of protein concentrations and saturated at 0.02 mg/mL. The lower detection limit of the sensor was on the order of ng/mL and may be further improved by optimizing the device structure. This sensor may be used for detecting various proteins by decorating TRGO sheets with selected Au NP-antibody conjugates. The sensor may be capable of detecting a variety of proteins for in vitro diagnostics.

Example 3

Thermal Reduction of GO Sheets

Figure 3:
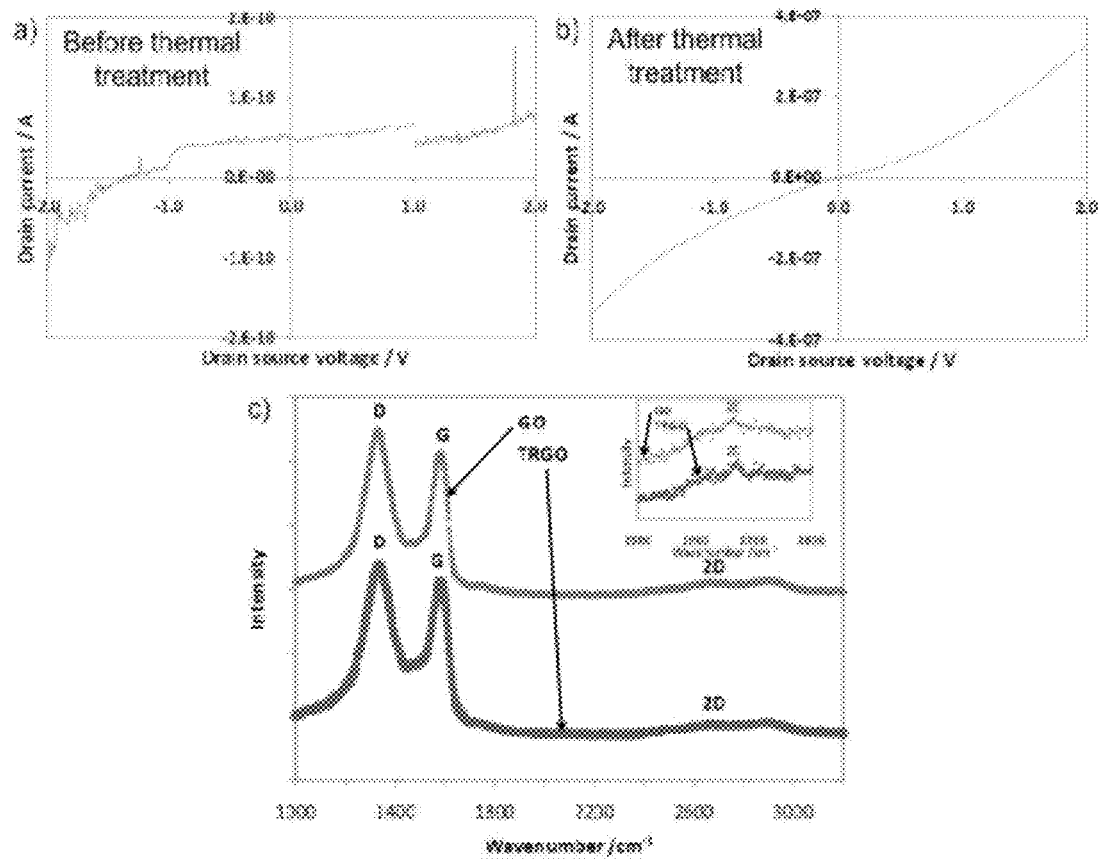
FIG. 3 shows drain-source voltage dependence of the drain current $I_d$ for graphene oxide (GO) FETs before (a) and after (b) the thermal treatment in argon flow at 200° C. for one hour. It is expected that part of the oxygen groups on GO sheets were removed during the thermal treatment. Similar thermal reduction of the GO sheet has been reported in argon flow at 200° C. for 30 minutes, through which the atomic ratio of carbon to oxygen in the GO sheet increased from 2.8 to 3.9.

The GO sheet included a hexagonal ring-based carbon network having both $sp^2$-hybridized and $sp^3$-hybridized carbons bearing hydroxyl and epoxide functional groups on either side of the sheet, whereas the sheet edges are mostly decorated by carboxyl and carbonyl groups. The extensive presence of saturated $sp^3$ bonds, the high density of electronegative oxygen atoms bonded to carbon, and other "defects" give rise to an energy gap in the electron density of states and makes GO sheets non-conductive. However, the structural and electronic properties of GO sheets can be modified by a variety of chemical and thermal processes (Park et al., Chem. Mat. (2008) 20:6592; Park et al., Nat. Nanotechnol. (2009) 4:217). A thermal treatment to the GO sheet was carried out in an argon flow at 200° C. for 1 hr and the GO sheet was partially reduced to the conductive TRGO sheet to be used as the electrical conducting channel in the FET. The thermal reduction of GO sheets was evidenced by the decrease of the GO device resistance from approximately 20,000 MΩ to approximately 2-20 MΩ and by the reduced Raman intensity ratio $I_{2D}/I_G$ from 0.15 to 0.06 (FIG. 3).

Example 4

Characterization and Use of TRGO FET

Figure 5:
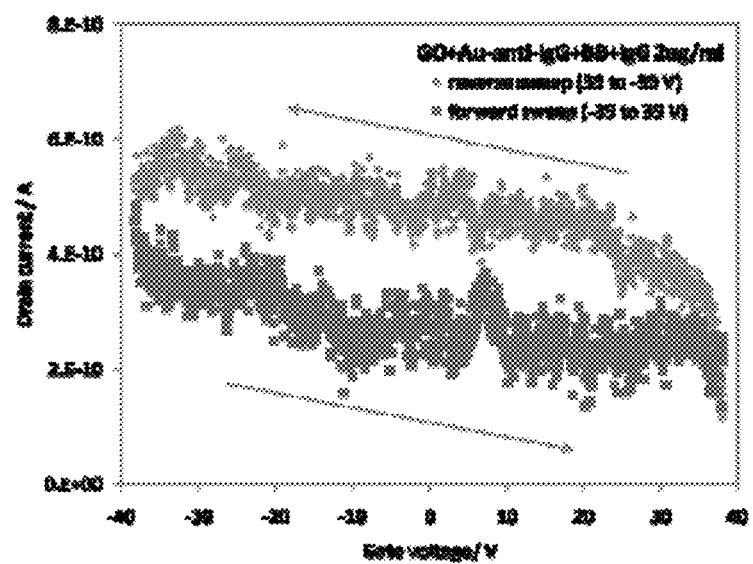
FIG. 5 shows the hysteresis response of the gate voltage dependence ($V_d$=0.1 V) of the drain current $I_d$ when the TRGO FET device is treated with IgG (2 μg/mL) at the final sensing step.

FIG. 12(a) shows the typical gate voltage dependence of the drain current $I_d$ from TRGO FETs treated with Au NP-anti-IgG conjugates, BB, and IgG (2 µg/mL). The gate voltage dependence of the drain current $I_d$ for the TRGO was typically p-type. TRGO sheets exhibited ambipolar and almost symmetric behavior for the electron and hole doping regions under vacuum, which was similar to graphene. However, exposure of TRGO sheets to the ambient environment led to the change of the device to p-type because of the adsorbed water and oxygen molecules on the TRGO sheet. With $V_g$ ramping from negative to positive, the drain current slowly decreased and a more significant current drop was observed around +35 V. However, due to the relatively small band gap of the TRGO, the on-off ratio of the FET device was small. Hysteresis effects commonly seen with CNT and graphene FETs, were observed and were mainly attributed to the polarization of adsorbed molecules (e.g., water vapor) in the applied electric field (FIG. 5).

Figure 4:
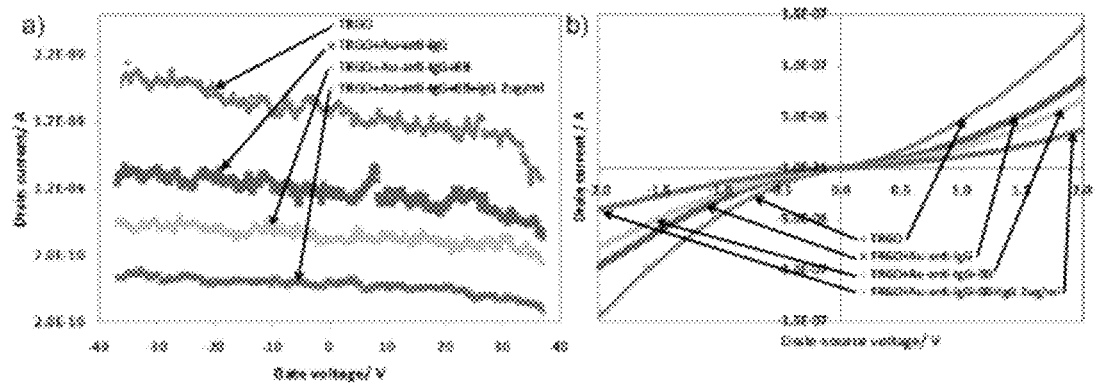
FIG. 4 shows the evolution of (a) typical gate voltage dependence ($V_d$=0.1 V) and (b) drain-source voltage dependence ($V_g$=0 V) of the drain current $I_d$ when the TRGO FET device is treated with Au NP-anti-IgG conjugates, blocking buffer (BB), and IgG (2 μg/mL). With the introduction of the target protein (IgG), a significant sensing response (decrease) in the $I_d$ was observed due to the binding of IgGs to anti-IgGs.

During the sensing process, it was found that the type of the device did not change; however, the drain current $I_d$ decreased with the addition of Au NP-anti-IgG conjugates, BB, and IgG. With the introduction of the target protein (IgG), a significant decrease in $I_d$ was observed (36.4% from the TRGO treated with Au NP/anti-IgG conjugates and BB). A controlled experiment was performed by introducing only the PBS buffer to the device and a much smaller sensor response (9.0% decrease in $I_d$) was observed, confirming that the significant sensor response mainly resulted from the binding of IgGs to anti-IgGs. The drain-source voltage dependence of the drain current $I_d$ of the sensor was investigated for protein binding (FIG. 4(b)). Consistent with the data shown in FIG. 4(a), the conductivity of the TRGO FET decreased after the addition of Au NP/anti-IgG conjugates, BB, and IgG, respectively. Drain-source voltage dependence of $I_d$ of the TRGO sheet was slightly non-linear. Similar thermal treatment may effectively lower the Schottky barrier present at the metal/TRGO interface so that the contact was nearly Ohmic. The nonlinearity was likely attributed to the carrier injection during the I-V measurement.

The observed electrical conductivity change in the TRGO FET could be attributed to two mechanisms. The binding of IgGs to anti-IgGs could lead to the local geometric deformation and increases the number of scattering centers across the sheet; thereby reducing the mobility of holes as well as the sheet conductivity, which was one of the sensing mechanisms in the CNT protein biosensor (Star et al., Nano Lett. (2003) 3:459). The sensing response was attributed to the p-type characteristic of the TRGO FET device. IgG includes four peptide chains (two heavy chains and two light chains) and the amine groups at the end of the chains are positively charged. Therefore, the attachment of a positively charged molecule, such as IgG, to the TRGO device was equivalent to a positive potential gating that leads to a reduced hole density and thus electrical conductivity of TRGO. Further studies are described below that reveal more details of the sensing mechanisms.

Figure 6:
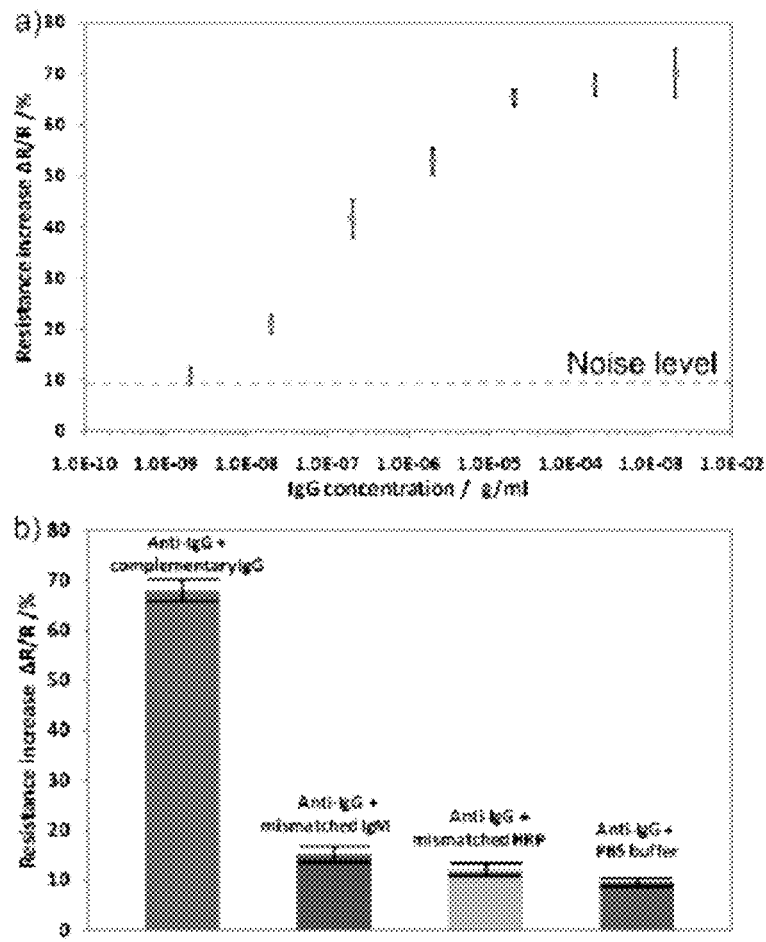
FIG. 6(a) shows the sensor sensitivity (relative resistance change, %) vs. the IgG concentration (g/mL) with $V_d$=2 V and $V_g$=0 V. Dashed line represents the noise level (9.8%) from the buffer solution.
FIG. 6(b) shows the comparison of the sensor sensitivity in response to complementary IgG (0.2 mg/mL), mismatched IgM (0.8 mg/mL), mismatched horseradish peroxidase (HRP) (0.2 mg/mL), and PBS buffer. Error bars were obtained through multiple measurements within the same test.

The sensor sensitivity (relative resistance change, %) as a function of the IgG concentration (g/mL) is presented in FIG. 6(a). The lowest IgG concentration level that was detected (10.8% resistance increase) and differentiated from the noise level was about 2 ng/mL, which represents the lower detection limit of the sensor. Similar to the nonlinearity behavior of CNT sensors, the sensor response increased non-linearly with the increase of the IgG concentration from 2 ng/mL to 0.02 mg/mL, which clearly showed that the sensor response was directly from the binding of IgGs to anti-IgGs and the level of sensor response depended on the IgG concentration. With more IgGs binding to anti-IgGs on the TRGO, more significant carrier mobility change in the TRGO sheet and larger gating effect were expected, thereby leading to more conductivity change in the FET device. When the IgG concentration reached 0.02 mg/mL, the sensor response was saturated and further increases in the IgG concentration from 0.02 to 2 mg/mL only led to slight changes in the sensor resistance. This phenomenon indicated that at 0.02 mg/mL concentration level, most of the binding sites (anti-IgG) on the TRGO sheet were occupied by target proteins. The working range of the sensor may be controlled by varying the areal density of Au NP-antibody conjugates on the TRGO sheet and by varying the number of antibodies on each Au NP.

Figure 7:
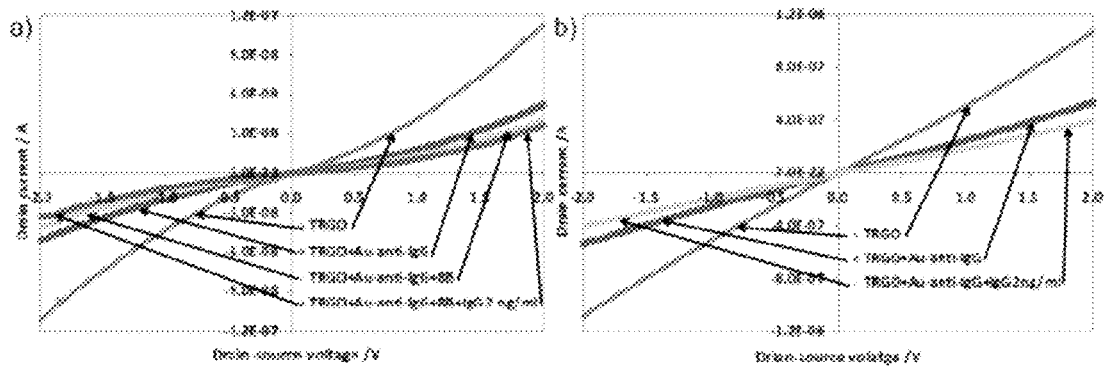
FIG. 7 shows the drain-source voltage dependence of the drain current $I_d$ for the TRGO FETs treated with Au NP/anti-IgG conjugates and IgG (2 ng/mL) with (a) and without (b) BB.

The blocking efficacy was evaluated by sensing 2 ng/mL IgG with and without BB. FIG. 7 shows the drain-source voltage dependence of the drain current $I_d$ for the TRGO FETs treated with Au NP/anti-IgG conjugates and IgG (2 ng/mL) with (a) and without (b) BB. Based on FIG. 7(a), the sensor response was very small (10.0% decrease in $I_d$) due to the very low concentration of the IgG (compared with 2 µg/mL IgG in FIG. 4(b)) and very small number of IgGs binding to the antibodies available in the TRGO FET. However, the $I_d$ decreased about 25.0% when the same 2 ng/mL IgG was added to the device without BB (FIG. 7(b)). The sensing response was not only from the binding of IgGs to anti-IgGs but also from the nonspecific binding of IgGs to TRGO sheets and electrodes, which led to the decrease in the electrical conductivity of the TRGO sheet. Results shown in FIG. 7 suggest that BB efficiently blocks the nonspecific binding of IgGs to the sensing element.

Treating the device with BB effectively diminished the undesirable response from the nonspecific binding of analytes to the device and allowed for the specific function of the sensor (FIG. 7). To verify the specificity of the sensor, IgM (0.8 mg/mL) and HRP (0.2 mg/mL) were used as mismatched proteins and introduced to the sensor with exactly the same procedure as that used for the IgG. Responses of the sensor are summarized in FIG. 6(b) for IgG, IgM, HRP, and the buffer solution. The sensor resistance change (response) from the mismatched IgM (15.3%) and HRP (12.4%) were significantly smaller than that from the complementary IgG (68.0%). This result further confirms that the sensor response was from the binding of IgGs to anti-IgGs and the target protein may be selectively detected by the TRGO FET sensor at low concentrations in the presence of mismatched/nonspecific proteins.

The reported sensor performance may be further improved by optimizing the TRGO FET device. The TRGO morphology, the number of TRGO sheets, the level of TRGO reduction, and the metal/TRGO interface may potentially influence electrical properties of the FET device and thus the sensor performance. The morphology (wrinkles, folds, number of layers) of the TRGO was determined by the quality of GO sheets and may be controlled by the GO preparation process. The number of GO sheets on the electrodes may be controlled by adjusting the concentration of the GO solution. The reduction level of TRGO was controllable through conditions used for the thermal treatment, such as treatment temperature, gaseous environment, and duration. The metal/TRGO interface was highly susceptible to modulations by adsorbed species and the Schottky barrier of the interface may lead to a significant change in the device conductance. Therefore, controlled thermal treatments may be used to effectively achieve the desired level of reduction in TRGO and to minimize the contact influence on the sensing response.

The dependence of the sensor response on the TRGO base resistance and the antibody areal density was systematically studied. A correlation was found to predict the sensor response as a function of the TRGO base resistance and the antibody areal density. With larger TRGO base resistance and higher antibody areal density, the sensor response was stronger. Along this line, the lower detection limit of the sensor was achieved at 0.2 ng/mL level by tuning the TRGO base resistance and the antibody areal density. Results from the parametric studies present a way to optimize the sensor structure for enhanced sensor performance. This sensor structure could be used in diagnostics for probing proteins with very low concentrations and is potentially useful in detecting different types of biomolecules using corresponding Au NP-biomolecule conjugates.

Example 5

Sensing Mechanism

Figure 8:
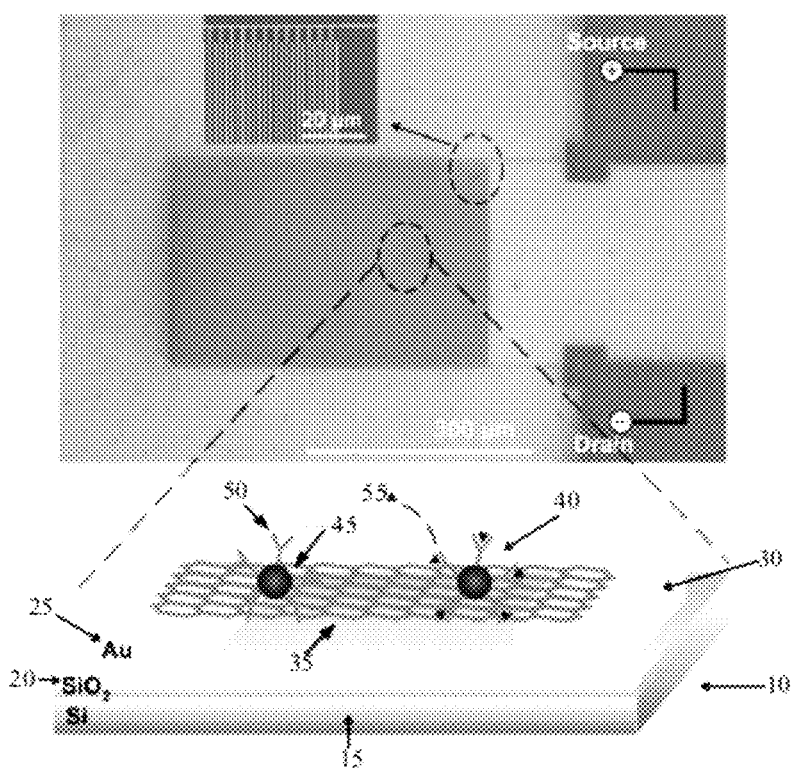
FIG. 8 shows an SEM image of Au electrodes on a silicon wafer with parallel gold fingers. A TRGO FET is accomplished by suspending TRGO sheets between the drain and the source electrodes; probe antibody is anchored to the TRGO sheet surface through Au NPs.

An SEM image of the Au sensor electrodes on a silicon wafer with parallel interdigitated fingers is shown in FIG. 8. The TRGO FETs 10 were fabricated through dispersing GO sheets 35 onto the sensor electrode so that GO sheets 35 spanned between the drain 30 and the source 25 electrodes. The GO sheet 35 was a carbon network with hydroxyl and epoxide groups on either side of the sheet, whereas with carboxyl and carbonyl groups on the sheet edges. The saturated sp3 carbon, the high density of electronegative oxygen atoms, and other "defects" gave rise to an energy gap in the electron density of states and made GO sheets non-conductive. In the Examples previously described above, thermal treatment to the GO sheet was carried out in an argon flow at 200° C. for 1 hr and it was found that the GO sheet 35 was partially reduced to the conductive TRGO sheet. In this Example, the GO sheets were reduced at 400° C. for 1 hr and the successful reduction of GO sheets was confirmed as evidenced by the resistance level of the TRGO devices (540Ω-3.6 MΩ). As shown in FIG. 8, the TRGO sheet 35 worked as the conducting channel in the sensor 10, while the antibody 50 was anchored to the TRGO surface 35 through Au NPs 45 and functioned as the probe protein. The binding site of an antibody was located in the Fab portion of the molecule and was constructed from the hypervariable regions of the heavy and light chains. At the molecular level, an antigen 55 was characterized by its ability to be "bound" at the antigen-binding site of an antibody 50 and antibodies 50 tended to discriminate between the specific molecular structures presented on the surface of the antigen 55. Thus, the antigen-antibody reactions were like a key (antigen 55) which fits into a specific lock (antibody 50). The bonds that hold the antigen 55 to the antibody binding site were non-covalent in nature, such as hydrogen bonds, electrostatic bonds, van der Waals forces, and hydrophobic bonds. The sensor configuration allowed the direct diffusion and binding of the target protein (antigen) to the probe protein (antibody) on the Au NP and the binding induced a conductivity change in the TRGO channel, which was measured by the drain current in FET and direct current measurements.

Figure 9:
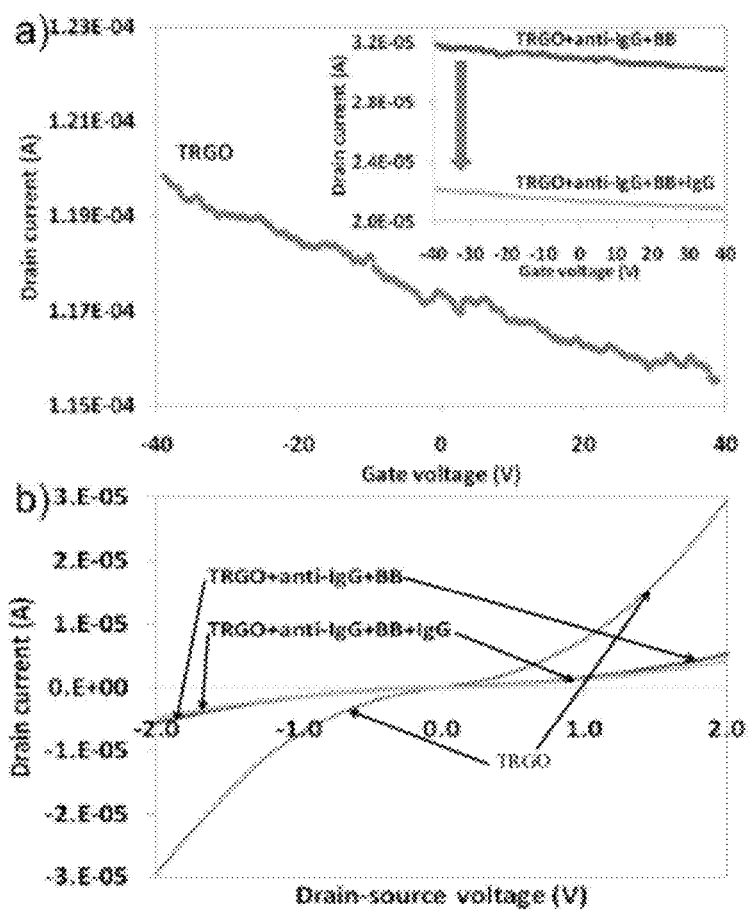
FIG. 9(a) shows the typical gate voltage dependence ($V_d$=5.0 V) of the drain current $I_d$ of the TRGO (sample GO3). Inset are the FET results of the sensor treated with Au NP-anti-IgG conjugates, BB, and IgG (2 ng/mL). The drain current decreased after the adding of IgG.
FIG. 9(b) shows the direct current measurement results of the TRGO (sample GO3) treated with Au NP-anti-IgG conjugates, BB, and IgG. The drain current decreased after the adding of IgG.

FIG. 9 shows the typical FET and I-V curves of the TRGO sensor treated with Au NP-anti-IgG conjugates and IgG (sample GO3 in Table 1). Table 1 shows the sensor parameters and responses to 2 ng/mL IgG using different NP sizes (10 and 20 nm) and different reduction conditions (400° C. and 200° C. in Argon for 1 hr). The uncertainty of the sensor responses was obtained from the forward and backward FET measurements (two sensors were tested for each sensing case).

TABLE 1

| Sample | Au NP size (nm) | GO reduction temperature (° C.) | TRGO resistance ($10^4$ Ω) | Au NP areal density (/$\mu m^2$) | Antibody areal density (/$\mu m^2$) | Sensor response (ΔR/%) |
|---|---|---|---|---|---|---|
| GO1 | 10 | 400 | 0.054 | 22.5 | 270.2 | 6.6 ± 0.9 |
| GO2 | 10 | 400 | 0.986 | 21.3 | 254.8 | 15.3 ± 2.5 |
| GO3 | 10 | 400 | 4.26 | 26.7 | 320.3 | 44.1 ± 5.5 |
| GO4 | 10 | 400 | 120 | 22.5 | 269.7 | 60.9 ± 11.7 |
| GO5 | 10 | 400 | 5.09 | 12.1 | 144.7 | 18.6 ± 6.4 |
| GO6 | 20 | 400 | 3.37 | 1.9 | 93.1 | 4.5 ± 1.6 |
| GO7 | 20 | 400 | 3.36 | 4.6 | 221.8 | 26.4 ± 1.2 |
| GO8 | 20 | 400 | 360 | 2.0 | 94.6 | 37.5 ± 6.4 |
| GO9 | 20 | 200 | 7.81 | 8.0 | 384.1 | 10.8 ± 1.6 |

The FET and I-V results of the 10 nm Au NP-antibody sensor were very similar to the results for the 20 nm counterparts (Mao et al., Carbon (2010) 48:479). The gate voltage dependence of the drain current $I_d$ of TRGO (FIG. 9(*a*)) shows that the TRGO was p-type; and with $V_g$ ramping from negative to positive, the drain current slowly decreased and the Dirac point of the transistor was beyond +40 V. The on-off ratio of the TRGO FET was small, which was mainly because the GO sheets were partially reduced and the FET test was performed in ambient environment. With the FET test in a vacuum, the on-off ratio of the TRGO was higher than that in the ambient environment and the TRGO was ambipolar (Jung et al., Nano Lett. (2008) 8:4283; Li et al., J. Am. Chem. Soc. (2009) 131:15939). In the sensing step (FIG. 9(*a*), inset), with the introduction of the IgG solution to the sensor, the drain current $I_d$ decreased, which may be explained by the increase of the electronic scattering centers on the TRGO sheet and the gating effect of the accumulated charges from IgG proteins. From the FET results, the slopes of the FET curves were almost the same before and after the introduction of IgGs, indicating that the attached IgGs had an insignificant effect on the carrier mobility in the TRGO. The change in the carrier density might be responsible for the resistance change in the TRGO, which may be evaluated by the Dirac point shift. To accurately evaluate the carrier density change, a new sensor structure with a single TRGO sheet with well-defined geometry was needed. The direct current measurement results (FIG. 9(*b*)) also indicated that the sensor resistance increased after the adding of IgG, which was in accord with the FET measurement results. Control experiments were performed on a pristine TRGO device (i.e., device without anti-IgG functionalization). The device resistance increased upon the introduction of 2 ng/mL IgG; however, the sensor signal from nonspecific binding of IgG to TRGO was much smaller than that from the binding of IgG to anti-IgG (i.e., device with anti-IgG functionalization).

Figure 10:
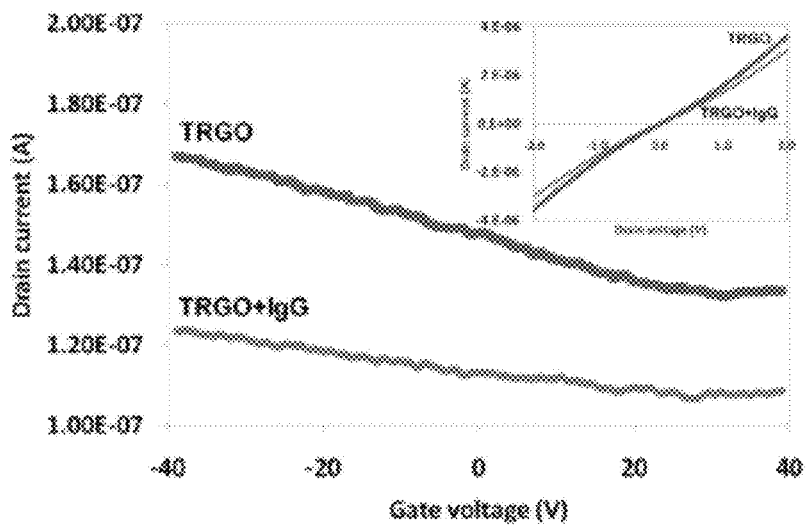
FIG. 10 shows FET curves ($V_d$=0.1 V) of a pristine TRGO device being exposed to 2 ng/mL IgG. The drain current decreased after adding IgGs. Inset are the Direct current measurement results of the pristine TRGO device treated with IgG. The drain current decreased after the adding of IgG.

The specificity of the sensor was also studied with non-specific proteins and the results showed that the sensor had much smaller response to nonspecific proteins and buffer solution. The FET and direct current measurement results are shown in FIG. 10. The device resistance change was about 26%. In addition to its nonspecificity, this response was much smaller than that from a sensor with the same TRGO resistance (R=7.2×105Ω) and high antibody areal density (250/μm2), which had a 55% sensing response for 2 ng/mL IgG. In the sensing platform reported here, the nonspecific binding was greatly diminished by treating the device with blocking buffer.

Because the resistance change in TRGO was used to describe the sensor signal and the binding of antibodies to antigens directly led to the sensor signal, these two parameters were chosen for parametric studies. Since the TRGO sheets were randomly dispersed on the electrodes, and the sheet size and the sheet layout were different for each sensor, it was difficult to precisely describe the configuration of the TRGO sheet simply using a single parameter such as the number of TRGO sheets or the surface area of TRGO sheets on the electrode. The overall sensor base resistance (before the Au NP-antibody assembly) was used to evaluate the TRGO sheet configuration, and the resistance value was representative of the overall geometric configuration of the TRGO sheet (e.g., the number of TRGO sheets, the number of layers in each TRGO sheet, the size of an individual TRGO sheet, and the layout of the TRGO sheet on the electrode). In general, a smaller sensor base resistance corresponded to a larger GO concentration before dispersion since more TRGO sheets resulted in more conducting channels in the FET sensor. The TRGO base resistance was controlled by adjusting the concentration of the GO solution. For the antibody areal density, since the number of antibodies on a single Au NP changed with the size of the Au NP, the antibody areal density on the TRGO was controlled by varying the Au NP size as well as the concentration of the Au NP-antibody colloidal solution.

To quantitatively evaluate the dependence of the sensor response on the TRGO base resistance and the antibody areal density, sensors with different parameters were tested and the results are summarized in Table 1. The sensor base resistance was calculated from the FET curve and the antibody areal density was obtained by the product of the Au NP areal density and the number of antibodies on each Au NP. There were approximately 12 antibodies on each 10 nm Au NP and 48 antibodies on each 20 nm Au NP. The Au NP areal density was defined as the number of Au NPs per unit surface area of the TRGO (per μm²), which was obtained by time-consuming SEM imaging analysis. For each sensor, SEM images were taken at randomly-picked locations on the electrodes, and the number of NPs and the surface area of TRGO sheets were measured directly from the images. The calculated Au NP areal density was the average value from different locations on the sensor.

From Table 1, the Au NP areal densities of the samples GO1-GO4 were similar, ranging from 21.3 to 26.7 μm²; but the sensor resistance increased from 5.40×10²Ω to 1.20×10⁶Ω. From the corresponding sensor responses, the sensor response increased with the increase of the TRGO base resistance, in which the amplitude of the response was enhanced nearly ten times from 6.6% to 60.9%. With the same IgG concentration and similar Au NP areal density (all 10 nm Au NP), the increase of the sensor response was attributed to the TRGO base resistance in the sensor or the GO concentration prior to the drop-casting. Low. TRGO base resistance (high GO concentration) led to the overlapping layout of the TRGO sheets between the Au electrodes, in which the underneath TRGO sheets did not directly contact the Au NP-antibody conjugates. In this case, the conductivity, of the underneath TRGO sheets remained unchanged during the protein sensing; therefore the overall relative change in the sensor resistance was smaller.

Figure 11:
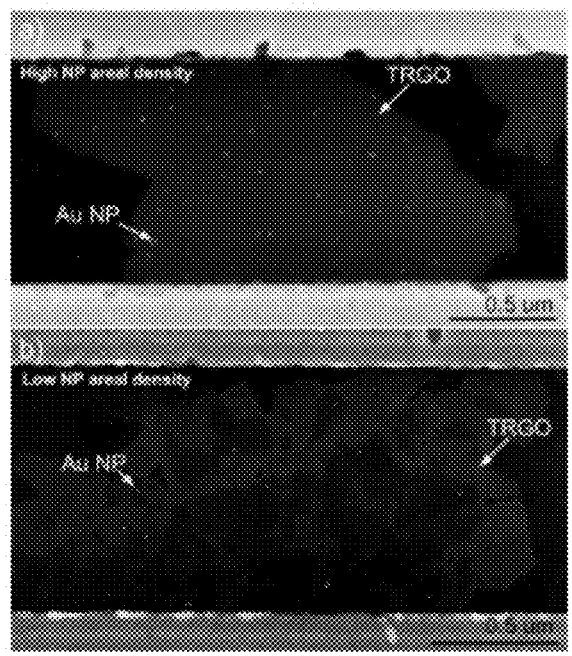
FIG. 11 shows SEM images of TRGO sheets functionalized with Au NP-antibody conjugates hanging between an electrode gap: a) sample GO2 with a high NP areal density; b) sample GO5 with a low NP areal density.

To study the antibody areal density influence on the sensor response, sample GO5 with a lower Au NP areal density was prepared. SEM images of the samples with high (GO2) and low (GO5) Au NP areal densities were compared and shown in FIG. 11. From the SEM images, single or multiple pieces of TRGO sheets were hanging between an electrode gap and the size of the TRGO sheets varied from hundreds of nanometers to one or two microns. Also, individual Au NPs were found uniformly distributed on the TRGO surface and no agglomeration of the NPs was observed. In our platform, the hybrid structure of Au NP-antibody conjugates immobilized on TRGO sheets were stable with several cycles of washing and drying as evidenced by SEM images. Based on TEM images, there were much more Au NPs on the TRGO sheets in sample GO2 than in sample GO5; and the calculated Au NP areal density was $21.3/\mu m^2$ for GO2 and $12.1/\mu m^2$ for GO5, respectively. In addition, the SEM images clearly showed the overlapping layout of the TRGO sheets between the Au electrodes and the underneath TRGO sheets were not functionalized with the Au NP-antibody conjugates, which further supports the previous discussion above on the TRGO base resistance and the sensor response.

By comparing sensing results from samples GO3 and GO5, which have similar TRGO base resistance ($4.26 \times 10^4$ and $5.09 \times 10^4 \Omega$) and different antibody areal density (320.3 and $144.7/\mu m^2$), the sensor response increased from 18.6 to 44.1% with higher antibody areal density. During the protein sensing, there may be more chance for target proteins to bind with antibodies on the TRGO with a higher antibody areal density, thereby leading to more antibody-antigen complex and thus larger response from the sensor.

Figure 12:
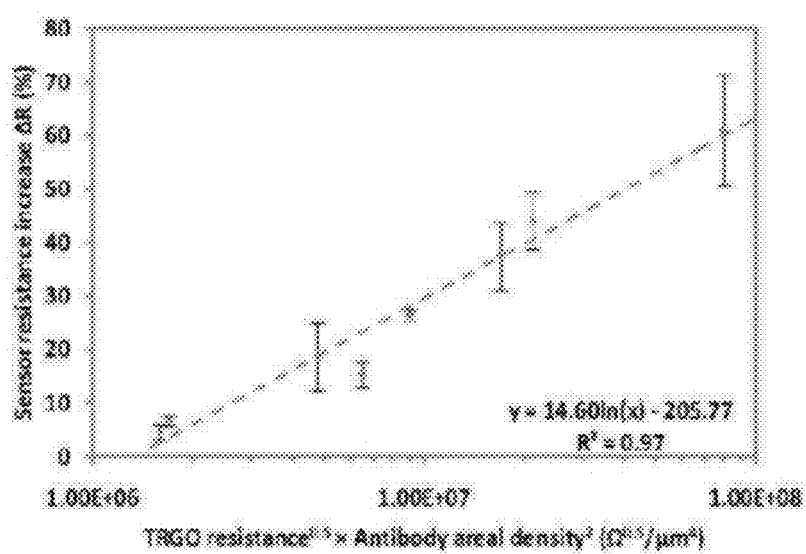
FIG. 12 shows sensor response (relative resistance change $\Delta R$, %) vs. TRGO resistance$^{0.5}$×antibody areal density$^2$ ($\Omega^{0.5}/\mu m^4$). Error bars were obtained through forward and backward FET measurements.

To quantitatively describe the dependence of the sensor response on the TRGO base resistance and the antibody areal density on the TRGO sheet, sensor response vs. TRGO resistance$^{0.5}$×antibody areal density² ($\Omega^{0.5}/\mu m^4$) was plotted in FIG. 12 for samples GO1-8 (both 10 and 20 nm Au NP-antibody conjugates). The trend line from the plotted points suggested that a correlation existed between the sensor response and the TRGO base resistance and the antibody areal density. The corresponding Eq. 1 shows the dependence of the sensor response on the sensor parameters, in which S is the sensor response, R is the TRGO resistance, D is the antibody areal density, and A, B are constants. The square root of TRGO resistance and the square of the antibody areal density were selected as the independent factors to obtain the best fit curve and the corresponding $R^2$ was 0.97. Based on the trend line, the calculated constants A and B were 14.60 and −205.77, respectively. This equation interprets that the sensor response increased with the increase of the TRGO base resistance and the antibody areal density.

$$S = d \times \ln(\sqrt{R} \times D^g) + B \qquad (1)$$

From Eq. 1, the sensor response to 2 ng/mL IgG may be estimated with known sensor parameters; however, if the sensor fabrication condition was different, e.g., with different GO reduction temperature, the equation should be modified. For instance, the sensor response to 2 ng/mL IgG using 20 nm Au NP-antibody conjugates with a GO reduction temperature at 200° C. was tested as 10.8% (sample GO9, Table 1), in which the TRGO base resistance was $7.81 \times 10^4 \Omega$ and the antibody areal density was around $384.1/\mu m^2$. Taking these values into the equation, the calculated sensor response was 50.8%, which was much larger than the tested sensor response. The difference between the calculated and tested sensor response may be explained by the inherent difference in the sensor fabrication condition. In sample GO9, the GO reduction temperature was 200° C., which was lower than that of samples GO6-8 (400° C.); and lower reduction level leads to higher TRGO base resistance and thus higher response from the prediction. When applying Eq. 1 to estimate the sensor response, the constants A and B should be modified according to different sensor fabrication conditions. Nevertheless, Eq. 1 successfully predicts the dependence of the sensor response on the sensor parameters for a particular situation and higher sensor response may be expected with larger TRGO base resistance and higher antibody areal density.

Figure 13:
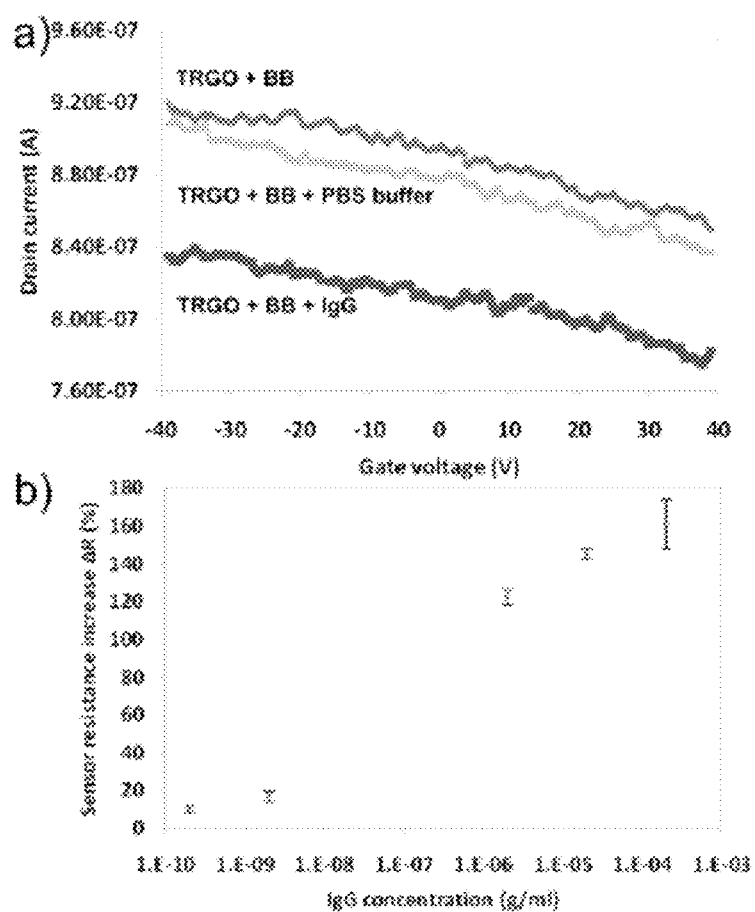
FIG. 13(a) shows FET curves ($V_d$=5.0 V) of the optimized sensor being exposed to PBS buffer and 0.2 ng/mL IgG. The drain current decreased after adding IgGs.
FIG. 13(b) shows sensor response (sensor resistance increase, %) vs. the IgG concentration (g/mL) obtained from FET sensing results of the optimized sensor. The detection limit of the optimized sensor was 0.2 ng/mL (10.3% sensor resistance increase). Error bars were obtained through forward and backward FET measurements.

To determine the sensor's lower detection limit using 10 nm Au NP-antibody conjugates, a sensor with large TRGO base resistance ($7.2 \times 10^5 \Omega$) and high antibody areal density ($229/\mu m^2$) was prepared, and the corresponding FET sensing curves to IgG-free PBS buffer and 0.2 ng/mL IgG are shown in FIG. 13(a). The FET curves show that the drain current decreased after adding PBS buffer and IgGs. PBS buffer lead to only 1.9% increase in the TRGO sensor resistance while the sensor response to 0.2 ng/mL IgG was 10.3%, which was larger than and was differentiated from the influence of the PBS buffer. Therefore, the lower detection limit of the new sensor was determined as about 0.2 ng/mL, which was one order lower than that of the non-optimized TRGO FET biosensors previously described above. The sensor sensitivity (relative resistance increase, %) as a function of the IgG concentration (g/mL) was also obtained from the optimized sensor and presented in FIG. 13(b). The sensor response increased non-linearly with the increase of the IgG concentration from 0.2 ng/mL to 0.2 mg/mL, which showed that the sensor response was directly from the binding of IgGs to anti-IgGs and the level of sensor response depended on the IgG concentration.

Based on Eq. 1, it was predicted that the lower detection limit of the sensor may be further improved. A sensor fabricated with a single piece of single-layer, large TRGO sheet having the highest antibody areal density that can possibly be achieved, i.e., the largest product of TRGO base resistance square root and the antibody areal density square, is predicted to have a better performance. To fabricate a single piece TRGO sheet FET sensor, the GO sheets is first deposited on the silicon wafer and then pattern Au electrodes are placed on the top of the single GO sheet. Alternatively, a highly dilute GO solution with extremely low concentration is prepared and drop-casted onto the Au electrodes to generate a single GO sheet bridging the electrode gap. The Au—NP antibody conjugates at higher concentrations while avoiding the agglomeration of NPs in the solution, would achieve a higher NP areal density on the TRGO sheet. The estimated antibody areal density limit in a closely packed model with the nanoparticle size and the corresponding antibody number on each nanoparticle was determined. The calculated antibody areal density limit was $1.28 \times 10^5/\mu m^2$ when using 10 nm Au NP. The quality of the GO sheet, the reduction level of the TRGO, and the TRGO/Au electrode interface may also be changed to influence the electrical properties of the TRGO FET and thus the sensor performance. These parameters can be controlled by annealing temperature and duration.

Example 6

TiN/NG Synthesis

The graphene oxide (GO) was synthesized via a modified Hummers method by using natural graphite as source (Kovtyukhova et al., Chem. Mater. (1999) 11:771; Hummers et al., Am. Chem. Soc. (1958) 80:1339). $C_3N_4$/GO was prepared by adding 10 mL 50% cyanamide solution (Sigma) into 100 mL graphene oxide solution (about 1.2 mg/mL) at 80° C. with continuous stirring until completely dry. The gray products were then heated at 400° C. for 1 hr to grow $C_3N_4$ polymer film on the surface of the GO ($C_3N_4$/GO). To prepare the TiN/NG, 1.0 g $C_3N_4$/GO powder was dispersed in 20 mL ethanol with the assistance of sonication; 1.5 mL tetrabutyl titanate was then added together with continuous stirring for 2 hr. The mixed products were then filtered and washed with ethanol and distilled water for twice, respectively. After drying at 80° C., the products were heated to 750° C. at a rate of 3° C./min under argon atmosphere and further annealed at 750° C. for 2 hr to evolve into the TiN/NG.

TaON/NG and GaN/NG were prepared through a similar procedure using $TaCl_5$ and $GaCl_3$, respectively, as the source. Specifically, 1.0 g $C_3N_4$/GO powder was dispersed in 20 mL ethanol solution with the assistance of sonication, and 1.5 mmol (about 0.54 g) $TaCl_5$ was added under vigorous stirring for 2 hr. After filtering and drying, the solid products were heat-treated using the same procedure as that for TiN/NG. And for the GaN/NG nanohybrids, 2 mmol (about 0.35 g) $GaCl_3$ was added into 20 mL 0.05 g/mL $C_3N_4$/GO suspension with continuous vigorous stirring for 2 hrs, and the subsequent treatment was the same as that used for above two nanohybrids. The nitrogen-doped graphene (NG) was prepared through annealing the $C_3N_4$/GO at 750° C. under argon atmosphere for 2 hr.

Example 7

Characterization of TiN/NG

The X-ray powder diffraction (XRD) patterns were conducted on a Bruker D8 diffractometer equipped with a scintillation counter and Cu KR radiation reflection mode. X-ray photoelectron spectroscopy (XPS) was carried out using VG ESCA 2000 with an Mg Kα as source and the C1s peak at 284.6 eV as an internal standard. The samples were characterized by using a Zeiss EM902 80 KV Filte transmission electron microscope (TEM) with Henry-Casting Energy, FEI Tecnai F20 ST 200 KeV high-resolution transmission electron microscope (HRTEM) and a LEO 1530 field emission scanning electron microscope (FESEM). $N_2$ adsorption-desorption measurements were carried out at 77 K using a Quantachrome Autosorb gas-sorption system.

Figure 14:
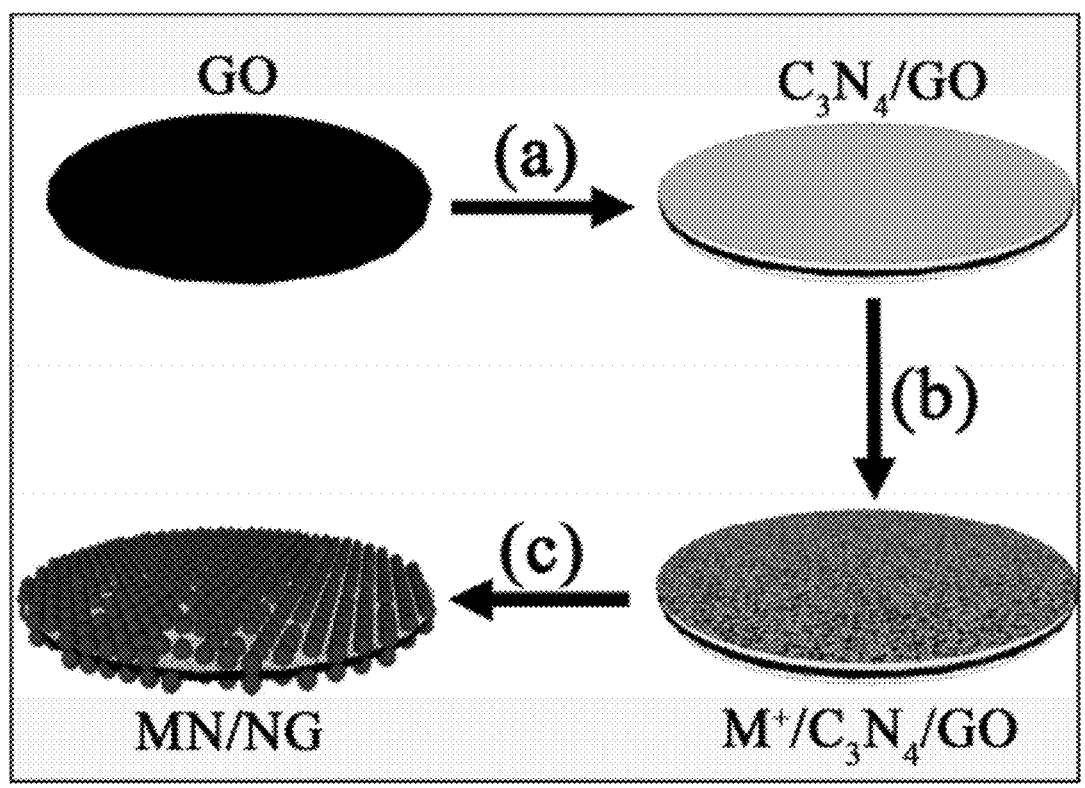
FIG. 14 shows a schematic illustration of the metal nitride/graphene nanohybrid synthesis process: (a) Polymerization of cyanamide on GO surface; (b) Adsorption of metal source in $C_3N_4$ polymer; (c) Reduction of GO and decomposition of $C_3N_4$ for nitrided reaction with formation of metal nitride on graphene.
Figure 15:
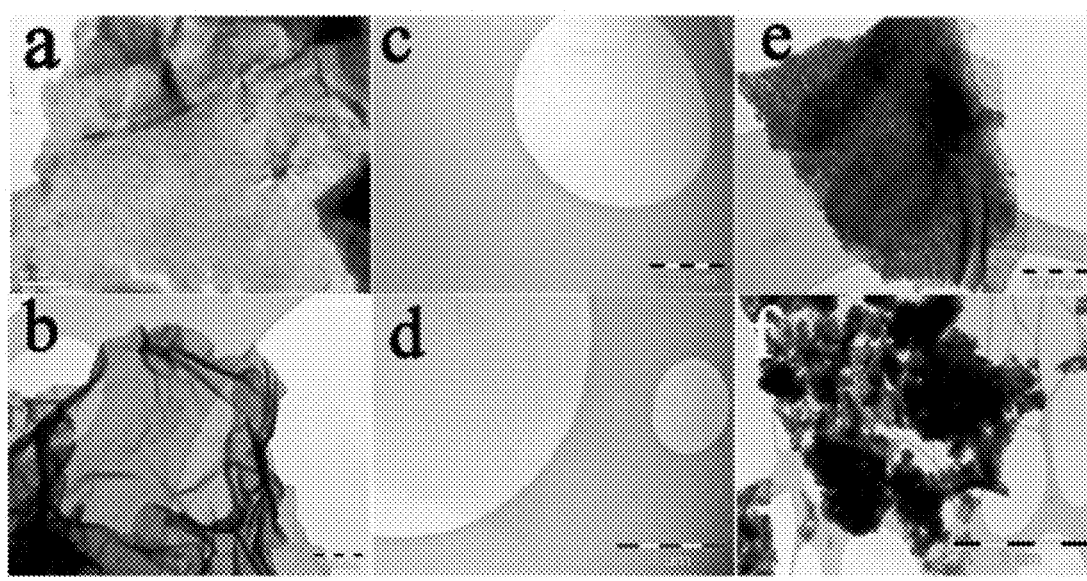
FIG. 15 shows a transmission electron microscope (TEM) images of TiN/NG (a, b), GO (c, d) and $C_3N_4$/GO (e, f).

FIG. 14 describes the procedure for typical synthesis of metal-nitride/NG nanohybrids. Firstly, a film of $C_3N_4$ polymer was coated on graphene oxide (GO) through initial aminations interaction between GO and cyanamide, which was followed by further polymerization of cyanamide on the GO surface. The $C_3N_4$/GO was then dispersed in aqueous or ethanol solution containing the metal source for effective adsorption of metal ions in the $C_3N_4$ polymer. The resulting product was then annealed to decompose $C_3N_4$ polymer to produce nitrogen-containing gases (Jun et al., Nat. Mater. (2009) 8:76), which finally led to reduction of GO, nitrogen doping in graphene, and the formation of metal-nitride nanoparticles on graphene (MN/NG) through nitrided reaction. Taking TiN/NG as an example, it was observed that, according to transmission electron microscopy (TEM) imaging, the contrast of TiN/NG (FIGS. 15(a) and 15(b)) fell between GO (FIGS. 15(c) and 15(d)) and $C_3N_4$/GO (FIGS. 15(e) and 15(f)), indicating the successful evolution from GO to $C_3N_4$/GO and finally to TiN/NG.

Figure 16:
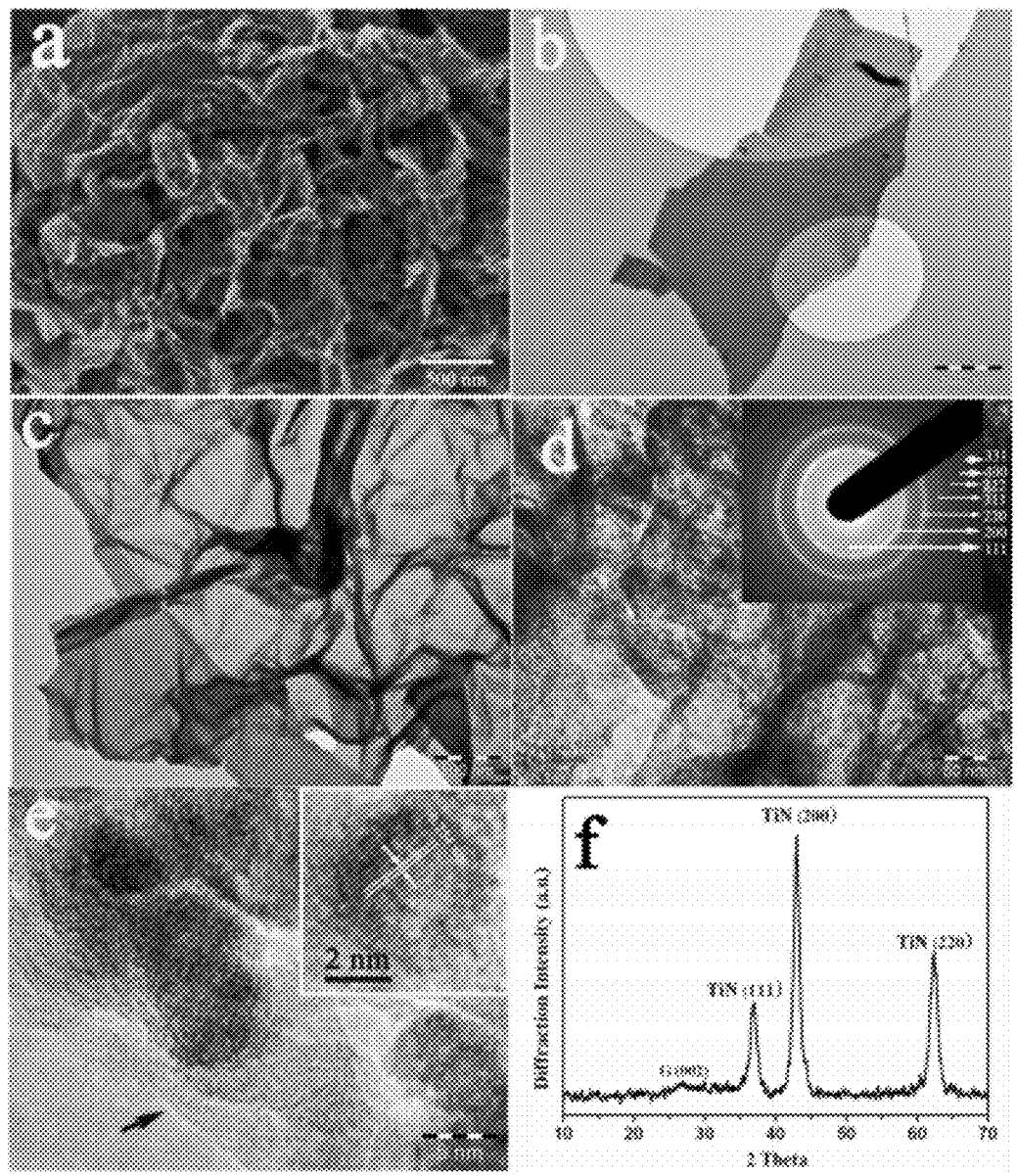
FIG. 16 shows an SEM image (a), TEM images (b-d), high-resolution transmission electron microscope (HRTEM) image (e), and X-ray powder diffraction (XRD) pattern (0 of the TiN/NG nanohybrids; inset of (d) is the corresponding SAED pattern and inset of (e) is a typical TiN nanoparticle on the NG surface.

The morphology of the as-prepared TiN/NG hybrid was examined using field-emission scanning electron microscopy (FESEM). The FESEM image in FIG. 16(a) presents an overview of the TiN/NG nanohybrids, revealing that the sample includes a flexural sheet structure. FIGS. 16(b) and 16(c) show TEM images of the TiN/NG nanohybrids with one sheet and several overlapping sheets, respectively, demonstrating that the nanohybrids well maintain the 2D structure of GO. A typical magnified TEM image of TiN/NG hybrids is shown in FIG. 16(d), in which one can observe that a large number of TiN nanoparticles are uniformly decorated on the graphene surface. The inset of FIG. 16(d) is the selected area electron diffraction (SAED) pattern of the TiN/NG nanohybrids, in which a series of well-defined rings was assigned to various diffraction planes of face-centered cubic (fcc) TiN. The crystallinity of TiN nanoparticles anchored on the NG was further examined through high resolution TEM (HRTEM) image shown in FIG. 16(e) and its inset. Well-defined crystalline lattice was observed with a spacing of 0.254 nm corresponding to (111) plane of TiN, and the diameter of a typical TiN nanoparticle was estimated as 4.7 nm. Additionally, the edge of the graphene was observed as indicated by the arrow.

Figure 17:
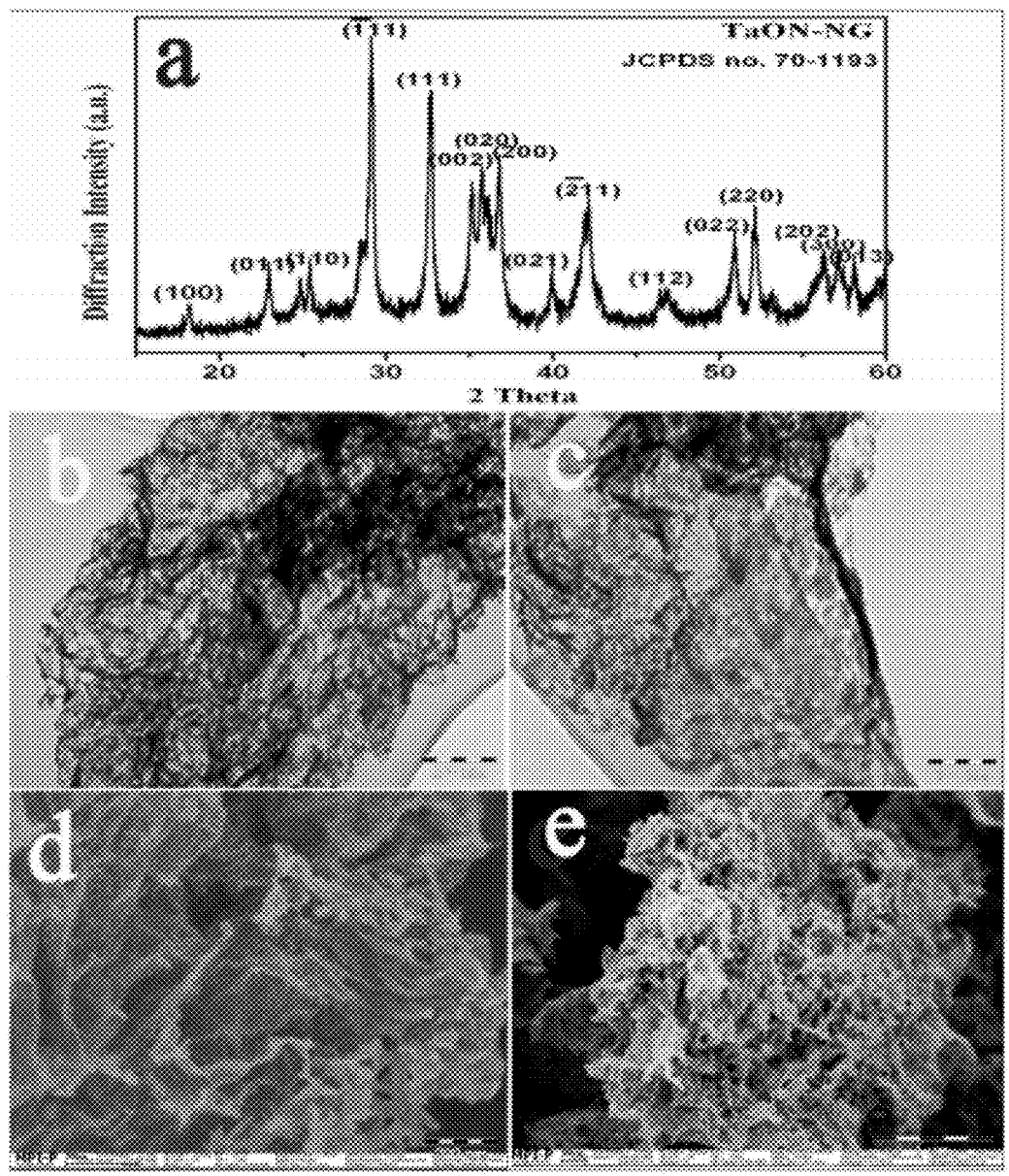
FIG. 17 shows an XRD pattern (a), TEM images (b, c) and SEM images (d, e) of TaON (monoclinic)/NG nanohybrids.
Figure 18:
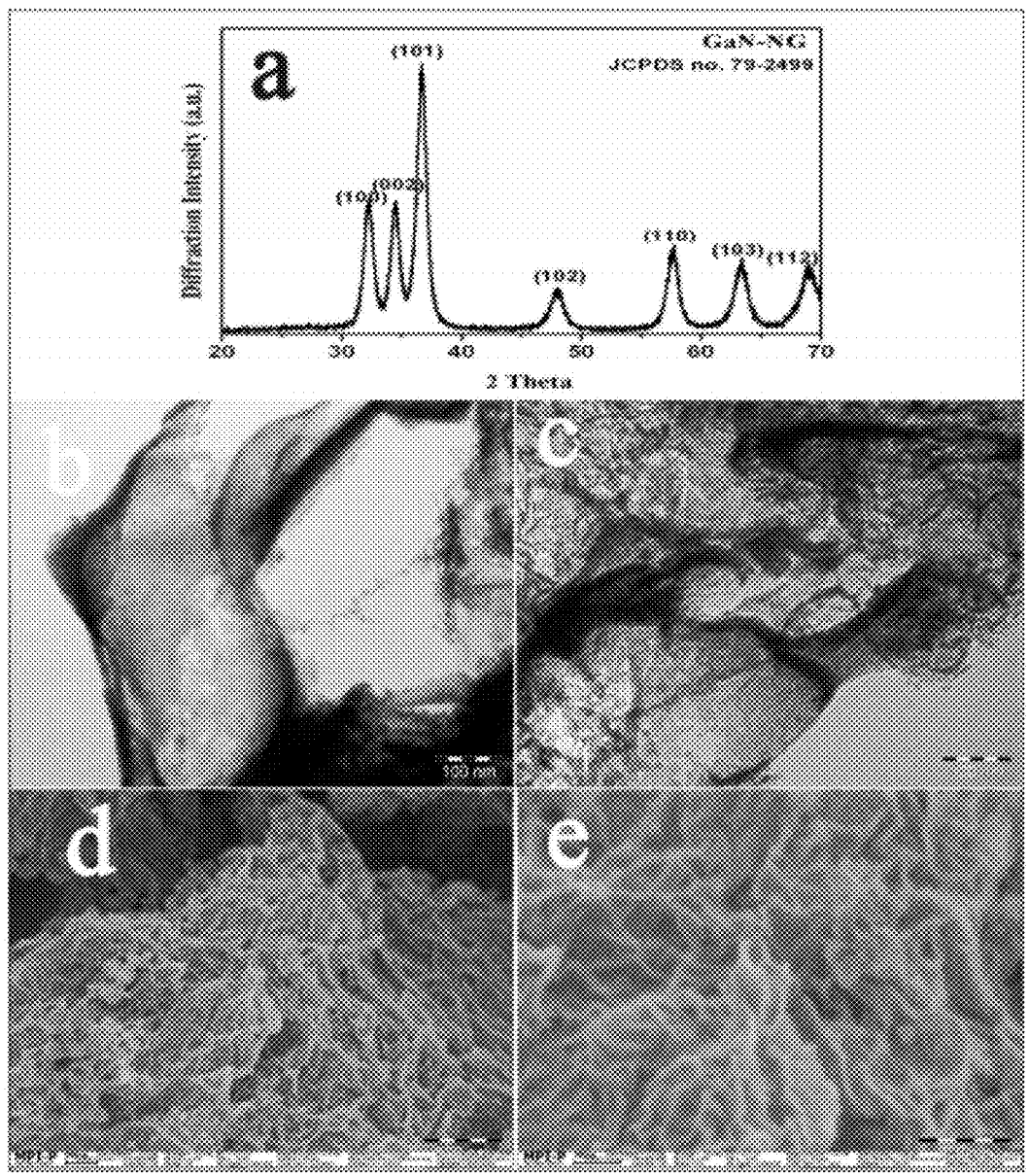
FIG. 18 shows an XRD pattern (a), TEM images (b, c) and SEM images (d, e) of GaN (hexagonal)/NG nanohybrids.

The crystallographic structure of the TiN/NG was further investigated by powder X-ray diffraction (XRD) (FIG. 16(f)). The crystallinity of TiN nanoparticles was evidenced by the diffraction peaks corresponding to (111), (200), and (220) peaks from fcc TiN (JCPDS no. 38-1420). According to the Scherrer formula (Scherrer, Nachr. Ges. Wiss. Göttingen 26: 98-100 (1918); Langford et al., J. Appl. Cryst. 11:102-113 (1978)), the average size of TiN nanoparticles was estimated to be 4.9 nm based on the half peak width of the TiN (200) peak, which was consistent with the HRTEM result. There are no other peaks present except for a weak peak at about 25.5° that corresponds to the (002) plane of NG sheets, suggesting that pure phase TiN was formed on the graphene surface during the synthesis process. The synthesis strategy may be extended to prepare other metal nitride modified graphene nanohybrids. For instance, using the similar method, TaON/NG (FIG. 17) and GaN/NG (FIG. 18) nanohybrids were prepared, in which both TaON and GaN nanoparticles was uniformly deposited on the graphene surface.

Figure 19:
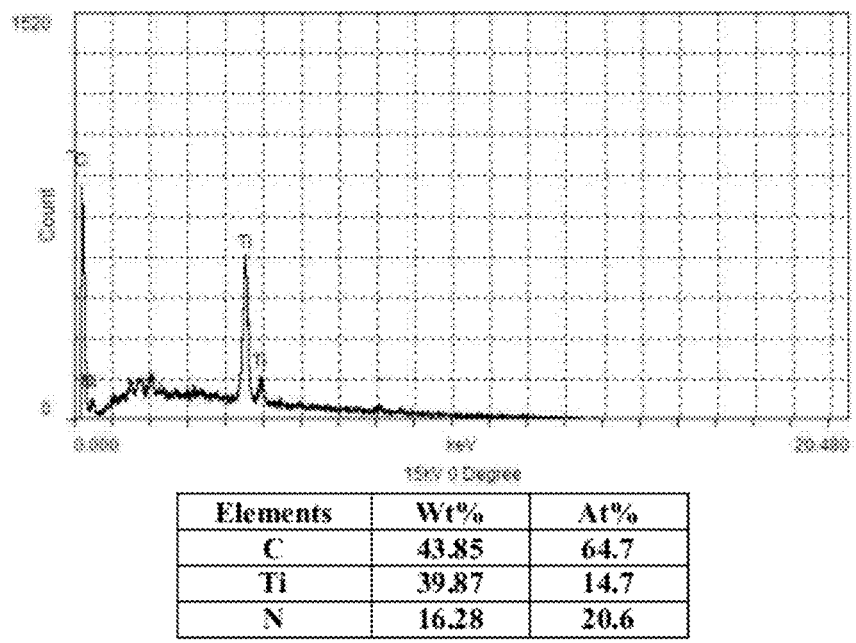
FIG. 19 shows an energy-dispersive X-ray spectroscopy of the TiN/NG.
Figure 20:
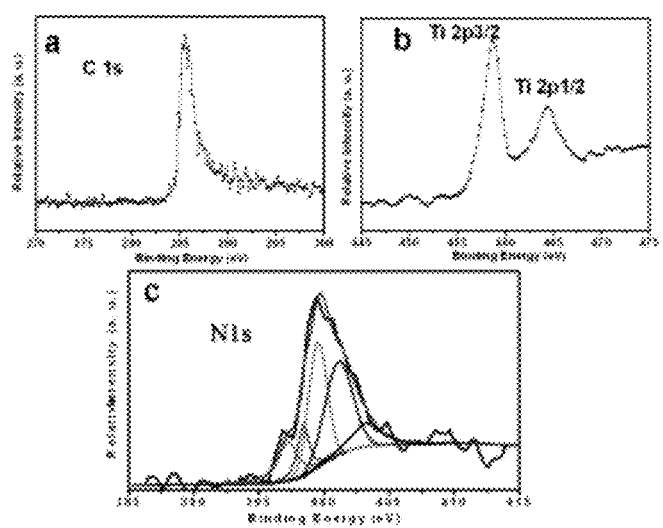
FIG. 20 shows a high-resolution X-ray photoelectron spectroscopy (XPS) spectra of TiN/NG hybrids showing Ti (2p), N (1s), and C (1s) peaks.
Figure 21:
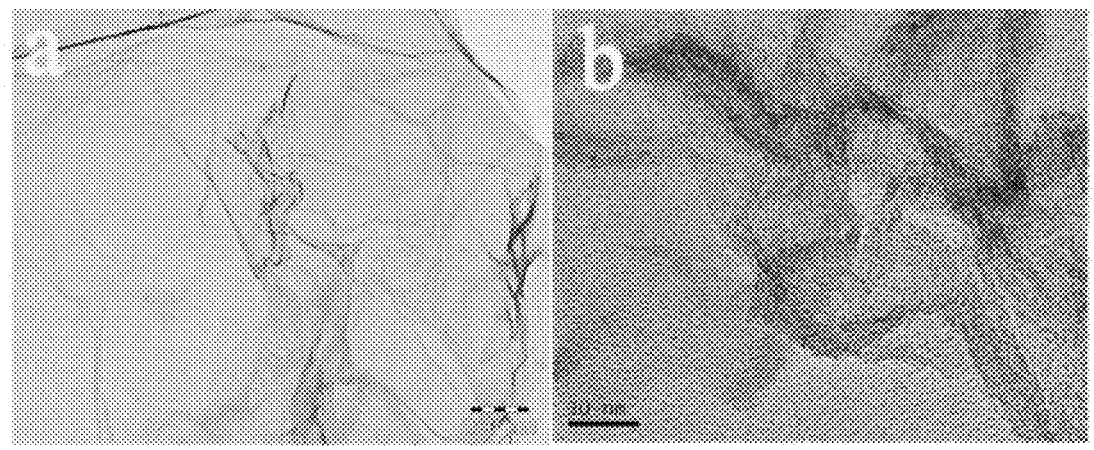
FIG. 21 shows a TEM images of NG prepared through annealing treatment of $C_3N_4$/GO.

Quantitative determination of the elemental composition was performed for TiN/NG samples by energy-dispersive X-ray spectroscopy (EDS, FIG. 19), revealing that the Ti:N:C elemental ratio was 1:1.4:4.4. Since XRD results confirmed that nanoparticles on graphene were pure phase TiN with a ratio of Ti:N=1:1, it was reasonable to estimate that the mass loading of TiN was as high as 51.5%. X-ray photoelectron spectroscopy (XPS) was further conducted to characterize the TiN/NG hybrids. FIGS. 20(a)-20(c) show the high-resolution N1s spectrum of Ti 2p, C 1s and N 1s respectively. The complex XPS N 1s spectra was fitted to five components of the binding energy. The binding energy at 397.2 eV was ascribed to nitridic N from TiN, while the other four curves corresponded to pyridine-like N (398.4 eV), pyrrole-like N (399.9 eV), graphite-like N (401.3 eV), and pyridine N-oxide (403.0 eV), respectively, indicating that these N species originated from doped N in NG. Based on the elemental analysis, the C/N molar ratio in NG was around 11. This result was in agreement with the pure phase NG samples (FIG. 21) synthesized by heat treatment of $C_3N_4$/GO.

Example 8

Catalytic Activity

The catalytic activity for NADH oxidation was performed using a three-electrode system, in which the Pt gauze and Ag/AgCl (3.0 M KCl) electrode were used as the counter electrode and the reference electrode, respectively. The glass carbon (GC) electrode was firstly polished using 0.3 and 0.05 μm alumina slurries. After washing with water and acetone, the GC was subjected to ultrasonic agitation for 2 min in ultrapure water. After drying, a homogenous suspension containing 2.5 mg/mL TiN/NG or NG was prepared by adding 2 mg samples into 1 mL 0.5% Nafion aqueous solution. 6.0 μL aliquot of this solution was then pipetted onto the surface of a freshly treated GC electrode by using a syringe. A beaker was covered over the electrode so that water evaporated slowly in air and a uniform film electrode was formed. Cyclic voltammetry were conducted in 0.1 M PBS (pH 7.0) solution containing different concentrations of NADH (beta-nicotinamide adenine dinucleotide, reduced $Na_2$-salt) at scan rate 50 mV/s. And time based amperometry was obtained at an applied potential of +0.1 V with successive addition of for NADH. For preparing the TiN/NG-LDH electrode, 0.1 mL of well-dispersed TiN/NG suspensions (2.5 mg/mL) were mixed with 0.1 mL D-lactate dehydrogenase solution (1.0 mg protein/mL), and 6.0 μL of the solution was drop cast onto the surface of a GC electrode to obtain TiN/NG-LDH electrode. The amperometry was conducted at an applied potential of +0.1 V with successive addition of lactate in 0.1 M PBS (pH 7.0) solution containing 5.0 mM NAD (beta-nicotinamide adenine dinucleotide).

Figure 22:
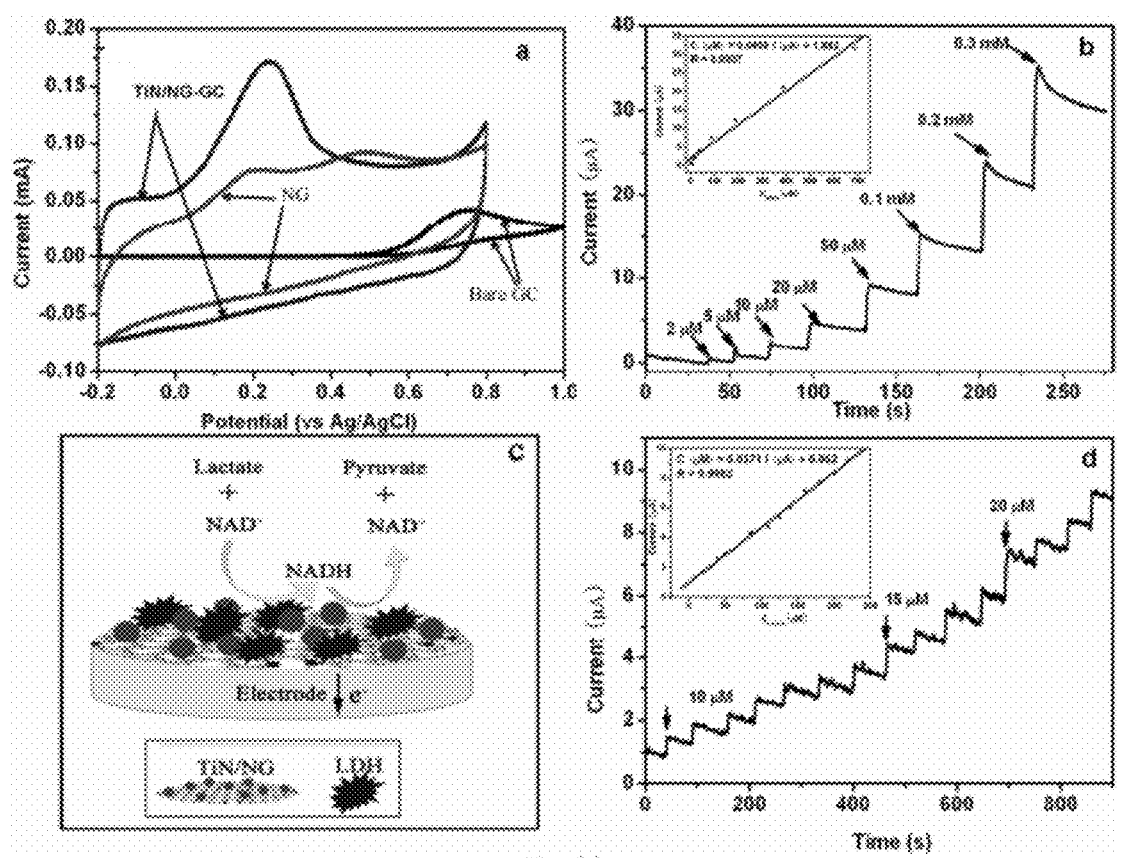
FIG. 22 shows (a) constant voltages (CVs) of porous TiN/NG, NG and bare GC electrodes in 0.1 M PBS (pH 7.0) solution containing 0.50 mM NADH in 0.1 M PBS solution at scan rate of 50 mV s$^{-1}$; (b) Successive amperometric response of the TiN/NG modified electrode to NADH in 0.1 M PBS (pH 7.0) at +0.10 V; (c) Schematic representation of the TiN/NG-LDH electrode for lactate detection; (d) Amperometric responses of TiN/NG-LDH modified GC electrode to successive addition of lactate in 0.1 M PBS (pH 7.0) at 0.1 V containing 5.0 mM NAD$^+$.
Figure 23:
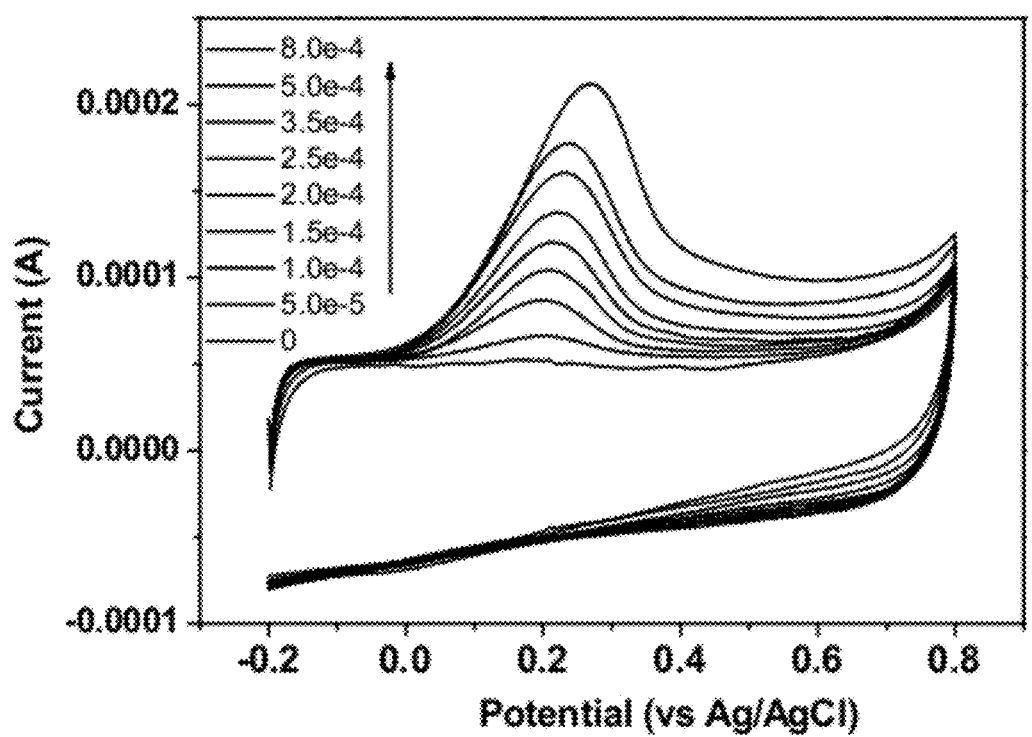
FIG. 23 shows CVs of porous TiN/NG electrodes in 0.1 M PBS (pH 7.0) solution containing different concentration of NADH in 0.1 M PBS solution, at a scan rate 50 mV s$^{-1}$.

The TiN/NG nanohybrids additionally showed excellent catalytic activity toward oxidation of NADH (nicotinamide adenine dinucleotide, reduced form). FIG. 22(a) presents the CVs of bare glass carbon (GC), NG, and TiN/NG modified electrodes in phosphate buffer solution (PBS, pH=7.0) containing 0.5 mM NADH recorded at 50 mV/s. Obviously, the TiN/NG electrode led to a remarkable increase of the peak current in comparison with the bare GC electrode and the NG electrode. Moreover, the peak potential markedly shifts from 0.76 V for the bare GC electrode to 0.23 V for the TiN/NG electrode, indicating a considerable decrease (by 0.53 V) in the overpotential of NADH oxidation reaction. Although the NG electrode also showed an anodic peak at around 0.25 V, the peak current was too small compared with TiN/NG electrode. As expected, the TiN/NG electrode brings forward a gradual increase of anodic peak current with the increase of the NADH concentration (FIG. 23), signifying that the TiN/NG electrode could provide a reliable platform for determination of NADH. FIG. 22(b) presents the typical amperometric response at the TiN/NG electrode with successive addition of different concentrations of NADH at an applied potential of +0.1 V, which shows a wide linear dynamic range from 2.0 to 687 μM with a correlation coefficient of 0.9937 and a high sensitivity of 0.0458 mA/mM. The detection of NADH is of great significance in the biosensor field because NADH is a side product of more than 300 $NAD(P)^+$ dependent dehydrogenase enzymes. Many important biological analytes can be determined by coupling the desired dehydrogenase enzyme with an effective detector of NADH. Therefore, the TiN/NG-LDH (lactate dehydrogenase) modified electrode was fabricated as a lactate biosensor (FIG. 22(c)), in which the electrochemical biosensor can respond to the addition of lactate since the lactate reacts with substrate ($NAD^+$) to generate NADH that was detected by the TiN/NG electrode.

As shown in FIG. 22(d), the successive addition of different amount of lactate gave rise to the proportional amperometric response in the range of 0.01 to 0.22 mM with the TiN/NG-LDH electrode. The regression equation of the calibration plot was C (μM)=0.037 I (μA)+2.05 with a correlation coefficient of 0.9982. In addition, the TiN/NG-GC electrode displayed a detection limit of $5×10^{-6}$ M with a signal/noise ratio of 2 and a response time of about 5 sec. All of the parameters indicated that the TiN/NG-LDH modified electrode was very effective as a biosensor for determining the lactate because the TiN/NG possesses excellent catalytic properties for NADH oxidation with high activity and low overpotential.

Example 9

Simulation Methods

Density functional theory (DFT) calculations were implemented in the simulation package flair (Weinert et al., Phys.: Condens. Matter (2009) 21:084201) using the all electron full potential linearized augmented plane wave (FLAPW) (Petersen et al., Computer Physics Communications (2000) 126:294) for the treatment of the core electrons interaction with the local density approximation (LDA) for the exchange and correlation. In all calculations, cutoffs of wave function and potential representations were 9.0 Ry and 144 Ry, respectively. Brillouin zone was sampled using an equivalent Monkhorst-Pack k grid of 12×12×12 for the graphene unit cell. The muffin tin radii for carbon, nitrogen and titanium atoms were 1.0, 1.0 and 2.0, respectively. To prevent the interaction between adjacent layers, a vacuum region of 20 Å was used in the vertical direction. All these parameters have been tested to obtain converged results. In the optimization process, positions of atoms were relaxed until the energy difference within two subsequent steps was less than $1×10^{-6}$. Hartree and the Hellman-Feynman forces on each nuclei was less than $1×10^{-4}$ Hartree/a.u. All the calculations were carried out in the graphene 2×2 cell with 8 carbon atoms. For the pure graphene, the lattice constant was fixed at the experimental value of 2.46 Å. A slab of 4-bilayers of alternating Ti and N atoms was used to simulate the bulk TiN crystal. In the super cell, the first layer of metal Ti contained 3 atoms, 1 sitting just above the center of graphene hexagon and the other 2 sitting at the atop sites. During the relaxation, the C atoms and size of super cell were fixed while the slab was allowed to fully relax.

Figure 24:
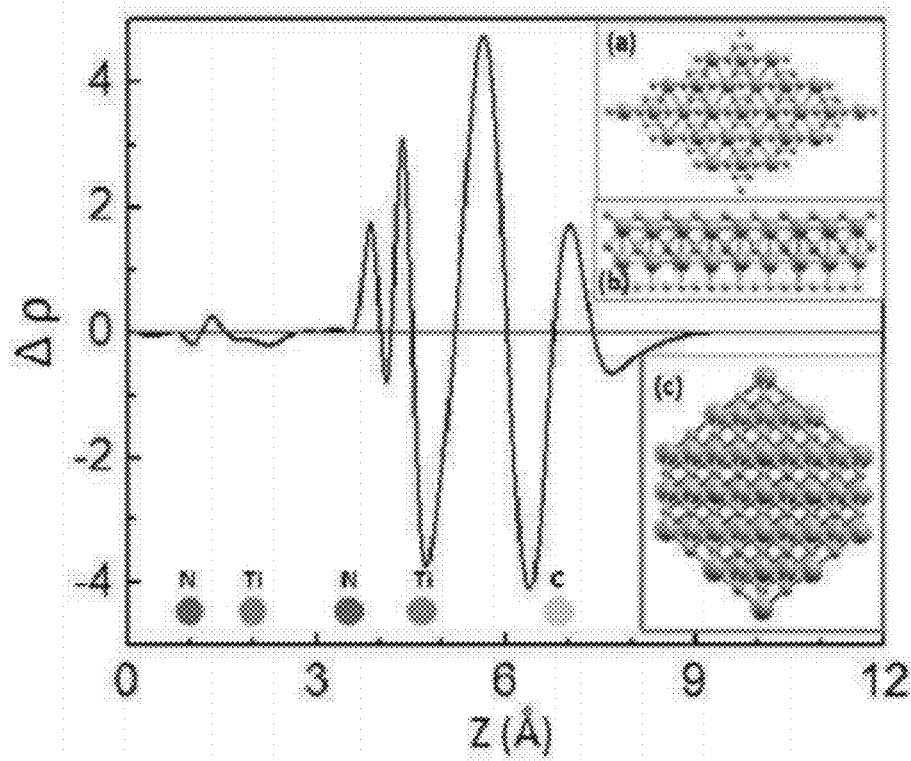
FIG. 24 shows a plane-averaged charge density difference along the vertical direction showing the electron redistribution upon formation of the graphene-TiN (111) interface at the Ti surface. Colored spheres indicate the positions of atom layers. Inset: (a) projected view of graphene and TiN (111) complex system; (b) and (c) are views along the (111) face for graphene-TiN (111) complex system and bulk TiN crystal.

The first-principle DFT calculations were performed to obtain better understanding of the multifunctional catalytic properties in the TiN/NG nanohybrids. The results suggest that Ti atoms of TiN can interact with the graphene to form chemisorption interfaces via metal carbide bonding. The plane-averaged charge density difference along the z axis likely pushed electrons into the middle region of the graphene and contacts TiN nanoparticles, which enabled the whole system to act metallically so that the electronic structure of graphene was disturbed (FIG. 24). Consequently, the TiN-graphene hybrids can provide the channel of electron transfer through orbital hybridization and thus show catalytic properties for electrochemical oxidation and reduction of some electroactive substrates.

Figure 25:
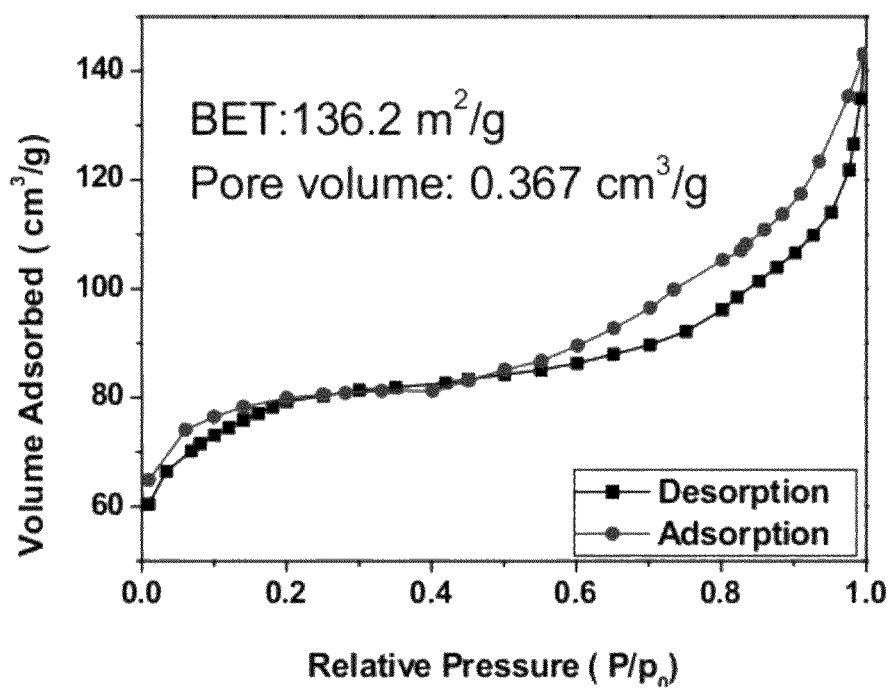
FIG. 25 shows a $N_2$ adsorption/desorption curve of TiN/NG nanohybrids.

Based on the above results, it appears that the electrocatalytic activity of TiN/NG mainly arises from synergetic effects between TiN and NG. In addition, TiN nanoparticles were uniformly decorated on the NG surface while maintaining a high surface area (136.2 $m^2$/g, FIG. 25). The uniform decoration and high surface area may provide reactants with more active sites in TiN nanoparticles. On the other hand, the excellent conductivity of NG provides a path for transferring electrons back and forth between the electrode and the external circuit, which may also play a key role toward the enhanced performance of TiN/NG-based biosensors.

Example 10

TiN/NG Nanohybrid FET-Based Biosensor

Gold interdigitated electrodes with both finger width and inter-finger spacing (source and drain separation) of about 1 μm and thickness of 50 nm are fabricated using an e-beam lithography process (Raith 150 lithography tool, 30 kV) on an Si wafer with a top layer of thermally-formed $SiO_2$ (thickness of 200 nm). TiN/NG nanohybrid sheets synthesized according to Example 6 are placed between the electrodes. One droplet (0.02 mL) of the TiN/NG nanohybrid suspension (0.6 mg TiN/NG/mL) is pipetted onto the electrodes and is dried under room temperature. The distance between the TiN/NG nanohybrid sheet and the $SiO_2$ surface is around 50 nm. The device is then annealed in argon flow (1 L/min) for 1 hr at 200° C. to reduce the TiN/NG nanohybrid sheets, remove residue solvents, and improve the contact between the TiN/NG nanohybrid sheets and electrodes. The Au NP-antibody conjugates are assembled onto the surface of the TiN/NG nanohybrid sheets using the drop casting method or ESFDA method described in Example 1. The TiN/NG nanohybrid FET-based biosensor is used to sense and detect proteins as described in Example 1.

We claim:

1. A field-effect transistor (FET)-based sensor, the sensor comprising: a nanostructure, nanoparticles in contact with the nanostructure, and one or more biomolecules in contact with the nanoparticles, wherein the nanostructure comprises a reduced graphene oxide sheet; and wherein the nanoparticles comprise gold.

2. The FET-based sensor of claim 1, wherein the nanostructure comprises a thermally-reduced graphene oxide sheet.

3. The FET-based sensor of claim 1, wherein the nanostructure comprises a metal nitride/graphene nanohybrid sheet.

4. The FET-based sensor of claim 3, wherein the metal nitride comprises titanium nitride (TiN), tantalum oxynitride (TaON) or gallium nitride (GaN).

5. The FET-based sensor of claim 4, wherein the metal nitride/graphene nanohybrid sheet comprises nitrogen-doped graphene (NG).

6. The FET-based sensor of claim 4, wherein the metal nitride/graphene nanohybrid sheet comprises TiN/NG.

7. The FET-based sensor of claim 1, wherein the biomolecule is selected from the group consisting of an DNA, protein, bacteria, virus, or fungi.

8. The FET-based sensor of claim 7, wherein the protein is one of an enzyme, a substrate, an antigen, an antibody, a ligand, an aptamer and a receptor.

9. The FET-based sensor of claim 8, wherein the protein comprises an antibody.

10. The FET-based sensor of claim 1, wherein the nanoparticle is in contact with the nanostructure by non-covalent bonding.

11. The FET-based sensor of claim 10, wherein the nanoparticle is in contact with the nanostructure by van der Waal forces.

12. A method of detecting a target biomolecule in a sample, the method comprising:
(a) contacting the FET-based sensor of claim 1 with a sample containing or suspected of containing the target biomolecule; and
(b) monitoring a change in an electrical characteristic.

13. The method of claim 12, wherein the change in an electrical characteristic as a function of time indicates the presence of the target biomolecule.

14. The method of claim 13, wherein the electrical characteristic is selected from the group consisting of conductance, capacitance, potential, resistance, and inductance.

15. The method of claim 13, wherein the sample is a gas sample or a liquid sample.

16. The method of claim 13, wherein the method detects a target biomolecule selected from the group consisting of an enzyme, a substrate, an antigen, an antibody, a ligand, an aptamer, a receptor, a nucleic acid, and a microorganism.

17. A method of making the FET-based sensor of claim 1, the method comprising:
depositing the one or more nanoparticles conjugated with the one or more proteins onto the nanostructure.

18. The method of claim 17, wherein the one or more nanoparticles are deposited onto the nanostructure using electrospray and electrostatic force directed assembly (ESFDA) or drop-casting.

19. A field-effect transistor (FET)-based sensor, the sensor comprising: a nanostructure, nanoparticles electronically coupled to the nanostructure, and one or more probe molecules in contact with the nanoparticles, wherein the nanostructure comprises a reduced graphene oxide sheet, and wherein the nanoparticles comprise gold.

* * * * *